US009687542B2

(12) United States Patent
Dodd et al.

(10) Patent No.: US 9,687,542 B2
(45) Date of Patent: Jun. 27, 2017

(54) RIFT VALLEY FEVER VIRUS REPLICON PARTICLES AND USE THEREOF

(71) Applicant: THE UNITED STATES OF AMERICA AS REPRESENTED BY THE SECRETARY OF THE DEPARTMENT OF HEALTH AND HUMAN SERVICES, Washington, DC (US)

(72) Inventors: Kimberly A. Dodd, Decatur, GA (US); Brian H. Bird, Atlanta, GA (US); Cesar G. Albarino, Atlanta, GA (US); Stuart T. Nichol, Atlanta, GA (US)

(73) Assignee: The Government of the United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 14/408,389

(22) PCT Filed: Jun. 18, 2013

(86) PCT No.: PCT/US2013/046250
§ 371 (c)(1),
(2) Date: Dec. 16, 2014

(87) PCT Pub. No.: WO2013/192144
PCT Pub. Date: Dec. 27, 2013

(65) Prior Publication Data
US 2015/0196630 A1 Jul. 16, 2015

Related U.S. Application Data

(60) Provisional application No. 61/661,614, filed on Jun. 19, 2012.

(51) Int. Cl.
| | | |
|---|---|---|
| *C12N 7/00* | (2006.01) | |
| *A61K 39/12* | (2006.01) | |
| *G01N 33/569* | (2006.01) | |
| *A61K 39/00* | (2006.01) | |

(52) U.S. Cl.
CPC ............... *A61K 39/12* (2013.01); *C12N 7/00* (2013.01); *G01N 33/56983* (2013.01); *A61K 2039/5254* (2013.01); *A61K 2039/5258* (2013.01); *C12N 2760/12223* (2013.01); *C12N 2760/12232* (2013.01); *C12N 2760/12234* (2013.01); *C12N 2760/12251* (2013.01); *C12N 2760/12252* (2013.01); *C12N 2760/12271* (2013.01); *G01N 2469/20* (2013.01)

(58) Field of Classification Search
CPC ............... A61K 2039/53; C12N 15/86; C12N 2760/12234; C12N 2710/10343; C12N 2710/14043; C12N 2740/15034; C12N 2740/16034; C12N 2760/12233; C12N 2760/12251; C12N 2760/16034; C12N 2760/16234; C12N 2770/36134; C12N 2760/12043; C12N 2760/12051; C12N 2740/13043; C12N 2740/13045
See application file for complete search history.

(56) References Cited

U.S. PATENT DOCUMENTS

| | | | |
|---|---|---|---|
| 5,804,372 A | 9/1998 | Cochran et al. | |
| 8,084,248 B2 | 12/2011 | Makino et al. | |
| 8,673,629 B2* | 3/2014 | Bird ..................... | A61K 39/12 424/93.2 |
| 9,109,199 B2* | 8/2015 | Kortekaas .............. | A61K 39/12 |
| 2007/0122431 A1 | 5/2007 | Makino et al. | |
| 2011/0123567 A1* | 5/2011 | Bird ..................... | A61K 39/12 424/205.1 |
| 2013/0236493 A1* | 9/2013 | Kortekaas .............. | A61K 39/12 424/204.1 |

FOREIGN PATENT DOCUMENTS

| | | | |
|---|---|---|---|
| WO | WO2009082647 A2 | * | 2/2009 |
| WO | WO2009082647 | * | 7/2009 |

OTHER PUBLICATIONS

Bird et al. (C) J. Virol. Published on line Oct. 2011, vol. 85, No. 24, pp. 12901-12909.*
Brennan et al. J. Virol. published on Jul. 11, 2011, vol. 86, No. 19, pp. 10310-10318.*
Bhardwaj et al., "Vaccination with DNA Plasmids Expressing Gn Coupled to C3d or Alphavirus Replicons Expressing Gn Protects Mice against Rift Valley Fever Virus," *PLos Negl. Trop. Dis.*, vol. 4:e725, 2010.
Bird et al., "Rift Valley Fever Virus Lacking the NSs and NSm Genes is Highly Attenuated, Confers Protective Immunity from Virulent Virus Challenge, and Allows for Differential Identification of Infected and Vaccinated Animals," *J. Virol.*, vol. 82:2681-2691, 2008.
Bird et al., "Breaking the Chain: Rift Valley Fever Virus Control via Livestock Vaccination," *Curr. Opin. Virol.*, vol. 2:315-323, 2012.

(Continued)

*Primary Examiner* — Bao Li
(74) *Attorney, Agent, or Firm* — Klarquist Sparkman, LLP

(57) ABSTRACT

Disclosed herein is a robust system for the reverse genetics generation of a Rift Valley fever (RVF) virus replicon particle ($VRP_{RVF}$) vaccine candidate. $VRP_{RVF}$ can actively synthesize viral RNA and proteins, but lack structural glycoprotein genes, preventing spread within immunized individuals and reducing the risk of vaccine-induced pathogenicity. Is it disclosed herein that $VRP_{RVF}$ immunization is both safe and efficacious, resulting in a robust immune response that is protective against RVF virus challenge within 24 hours of immunization. Provided herein are $VRP_{RVF}$, methods of producing $VRP_{RVF}$, and method of using $VRP_{RVF}$ for immunization against RVF virus infection.

13 Claims, 6 Drawing Sheets

(56) References Cited

OTHER PUBLICATIONS

Bouloy et al., "Reverse Genetics Technology for Rift Valley Fever Virus: Current and Future Application for the Development of Therapeutics and Vaccines," *Antiviral Res.*, vol. 84:101-118, 2009.
Dodd, et al., "Single-Dose Immunization with Virus Replicon Particles Confers Rapid Robust Protection against Rift Valley Fever Virus Challenge," *J. Virol.*, vol. 86:4204-4212, 2012.
Gorchakov et al., Comparative Analysis of the Alphavirus-based Vectors Expressing Rift Valley Fever Virus Glycoproteins, *Virology*, vol. 366:212-225, 2007.
Heise, et al., "An Alphavirus Replicon-Derived Candidate Vaccine against Rift Valley Fever Virus," *Epidemiol. Infect.*, vol. 137:1309-1318, 2009.
Ikegami et al., "Rift Valley Fever Virus Nonstructural Protein NSs Promotes Viral RNA Replication and Transcription in a Minigenome System," *J. Virol.*, vol. 79:5606-5615, 2005.
Kortekaas et al., "Creation of a Non-Spreading Rift Valley Fever Virus," *J. Virol.*, vol. 85:12622-12630, 2011.
Kortekaas et al., "Efficacy of Three Candidate Rift Valley Fever Vaccines in Sheep," *Vaccine*, vol. 30:3423-3429, 2012.
LaBeaud, "Towards a Safe, Effective Vaccine for Rift Valley Fever Virus," *Future Virol*, vol. 5:675-678, 2010.

\* cited by examiner

Day 1　　Day 2　　Day 3　　Day 4　　Day 5

FIG. 2B

- VRP
- RVFV
- mock

Days post-infection

RIFT VALLEY FEVER VIRUS REPLICON PARTICLES AND USE THEREOF

CROSS REFERENCE TO RELATED APPLICATIONS

This is the U.S. National Stage of International Application No. PCT/US2013/046250, filed Jun. 18, 2013, published in English under PCT Article 21(2), which claims the benefit of U.S. Provisional Application No. 61/661,614, filed Jun. 19, 2012, which is herein incorporated by reference in its entirety.

FIELD

This disclosure concerns Rift Valley Fever virus replicon particles (VRPs), methods of making VRPs and their use as vaccines against Rift Valley Fever virus infection.

BACKGROUND

Rift Valley fever virus (RVFV) causes sporadic but devastating outbreaks of severe human disease and widespread morbidity and mortality in livestock. RVFV is a mosquito-borne virus of the Bunyaviridae family (genus *Phlebovirus*), and the timing of outbreaks is often closely associated with emergence of floodwater *Aedes* species mosquitoes following periods of extensive heavy rainfall (Schmaljohn and Nichol, Bunyaviridae, p. 1741-1789. In D. M. Knipe and P. M. Howley (ed.), Fields Virology, 5 ed. Lippincott Williams and Wilkins, Philadelphia, Pa., 2007). Although so far confined to Africa and the Arabian Peninsula, RVFV has the potential to spread to other parts of the world, given the presence and changing distribution of competent vectors throughout Europe and the Americas (Chevalier et al., *Euro. Surveill.* 15:19506, 2010; Elliott, *Clin. Microbiol. Infect.* 15:510-517, 2009; Turell et al., *J. Med. Entomol.* 47:884-889, 2010).

Livestock (e.g., sheep, cattle and goats) are particularly susceptible to RVFV disease; outbreaks are characterized by widespread abortion storms and neonatal mortality approaching 100% (Swanepoel and Coetzer, Rift Valley fever, p. 688-717. In J. A. W. Coetzer, G. R. Thomson, and R. C. Tustin (ed.), Infectious Diseases of Livestock with Special Reference to South Africa. Oxford University Press, Cape Town, 1994). Infection in adult animals is associated with lower mortality, but the loss of a large proportion of young animals has serious economic impact. Humans usually become infected after handling aborted materials or other infected animal tissues, or through the bite of an infected mosquito. Although generally self-limiting, human infections can manifest as a serious febrile illness marked by myalgia, arthralgia, photophobia, and severe headache. In a small proportion of individuals, RVFV disease can progress to hepatitis, delayed-onset encephalitis or retinitis, or a hemorrhagic syndrome. Case fatality in severely afflicted individuals can be as high as 20% (Bird et al., *J. Am. Vet. Med. Assoc.* 234:883-893, 2009). Currently, there are no specific treatments for RVFV infection recommended in humans or other animals.

RVFV has a tripartite negative-sense single-stranded RNA genome. The large (L) segment encodes the viral polymerase. The medium (M) segment encodes the structural glycoproteins, Gn and Gc, as well as non-structural proteins, including a 78 kD protein and NSm, a virulence factor suggested to function by inhibiting apoptosis (Won et al., *J. Virol.* 81:13335-13345, 2007). The ambisense small (S) segment encodes, in the viral sense, the nucleoprotein (NP) that is required for RNA synthesis, and the non-structural NSs protein in the opposite orientation. NSs is the major RVFV virulence factor and functions to inhibit the host immune response (Bouloy et al., *J. Virol.* 75:1371-1377, 2001) by generalized downregulation of host transcription (Billecocq et al., *J. Virol.* 78:9798-9806, 2004; Le May et al., *Cell* 116:541-550, 2004), post-transcriptional degradation of protein kinase R (PKR) (Habjan et al., *J. Virol.* 83:4365-4375, 2009; Ikegami et al., *Ann. N. Y. Acad. Sci.* 1171 Suppl 1:E75-85, 2009), and repression of the interferon-β (IFN-β) promoter (Le May et al., *PLoS Pathogens* 4:e13, 2008). Previous work has indicated the importance of both NSm (Bird et al., *Virology* 362:10-15, 2007) and NSs (Barnett et al., *J. Virol.* 84:5975-5985, 2010; Vialat et al., *J. Virol.* 74:1538-1543, 2010) in determining virulence in vivo.

The impact of RVFV disease throughout Africa and the Arabian Peninsula, and the potential for viral spread elsewhere, provide strong incentives to develop safe, efficacious, and affordable vaccines. Examples of recently developed candidate vaccines include DNA-vectored (Bhardwaj et al., *PLoS Negl Trop Dis* 4:e725, 2010; Lagerqvist et al., *Virol. J.* 6:6, 2009; Lorenzo et al., *Vaccine* 28:2937-2944, 2010), virus-like particle (VLP) (de Boer et al., *Vaccine* 28:2330-2339, 2010; Mandell et al., *Virology* 397:187-198, 2010; Näslund et al., *Virology* 385:409-415, 2009), replicon particle (Kortekaas et al., *J. Virol.* 85:12622-12630, 2011), and live attenuated vaccines (Bird et al., *J. Virol.* 82:2681-2691, 2008; Dungu et al., *Vaccine* 28:4581-4587, 2010). VLP candidates show promise and remarkable safety, but generally require adjuvant and/or multiple immunizations for complete protection. In comparison, live attenuated vaccines are highly immunogenic, presumably due to viral replication in an immunized host. However, early live attenuated vaccines (Smithburn, MP-12) were associated with teratogenesis and abortion in livestock (Botros et al., *J. Med. Virol.* 78:787-791, 2006; Hunter et al., Onderstepoort *J. Vet. Res.* 69:95-98, 2002). More recently, a naturally occurring RVFV mutant (Dungu et al., *Vaccine* 28:4581-4587, 2010; von Teichman et al., *Vaccine* 29:5771-5777, 2011) and a reverse-genetics derived candidate (Bird et al., *J. Virol.* 85:12901-12909, 2011) have been shown to be both safe and efficacious in livestock.

SUMMARY

Described herein is a replication-competent but non-spreading Rift Valley fever virus, referred to herein as Rift Valley fever virus replicon particles ($VRP_{RVF}$). $VRP_{RVF}$ are capable of undergoing a single round of infection, but are unable to spread beyond the first infected cell due to the lack of the M genome segment encoding the viral glycoproteins Gn and Gc. It is disclosed herein that immunization with $VRP_{RVF}$ is both safe and efficacious, resulting in a robust immune response that is protective against wild-type RVFV challenge within 24 hours of immunization.

Provided herein are $VRP_{RVF}$ comprising RVF virus Gn and Gc glycoproteins, polymerase protein and nucleoprotein, and RVF virus L and S genome segments, wherein the $VRP_{RVF}$ does not contain an RVF virus M segment or any nucleic acid molecule encoding the Gn and Gc glycoproteins.

Also provided is a method of producing $VRP_{RVF}$ by transfecting a host cell with a plasmid containing an antigenomic copy of an RVF virus L segment; a plasmid containing an antigenomic copy of an RVF virus S segment; and a plasmid encoding RVF virus Gn and Gc glycoproteins; and culturing the cells for a period of time sufficient to produce $VRP_{RVF}$. $VRP_{RVF}$ produced by such a method are also provided.

Immunogenic compositions comprising the $VRP_{RVF}$ disclosed herein and a pharmaceutically acceptable carrier are also provided by the present disclosure.

Also provided is a method of eliciting an immune response against RVF virus in a subject by administering to the subject an effective amount of a $VRP_{RVF}$ or an immunogenic composition disclosed herein.

Further provided is a method of immunizing a subject against RVF virus infection by administering to the subject an effective amount of a $VRP_{RVF}$ or immunogenic composition disclosed herein.

Methods of using $VRP_{RVF}$ as an adjuvant to enhance immunogenicity of a heterologous vaccine, or as a vaccine vector to elicit an immune response against a heterologous protein, such as a viral antigen or tumor antigen, are further provided by the present disclosure. A method of treating cancer in a subject by administration of the $VRP_{RVF}$ disclosed herein is also provided.

Also provided is a method of differentiating a subject administered $VRP_{RVF}$ from a subject naturally infected with RVF virus by detecting the presence or absence of anti-nucleoprotein antibodies, and either anti-NSs or anti-NSm antibodies.

The foregoing and other objects, features, and advantages of the invention will become more apparent from the following detailed description, which proceeds with reference to the accompanying figures.

BRIEF DESCRIPTION OF THE DRAWINGS

FIGS. 1A-1B: Reverse genetics-derived $VRP_{RVF}$ are morphologically indistinguishable from wild-type RVFV. (FIG. 1A) Schematic of Rift Valley fever virus (RVFV) genome (top) and the reverse genetics system as used for virus replicon particle ($VRP_{RVF}$) production (bottom). (FIG. 1B) Negative stain electron microscopy images demonstrating the morphological similarity of RVFV particles (left) and $VRP_{RVF}$ particles (right).

FIGS. 2A-2B: $VRP_{RVF}$ cannot spread beyond initially infected cells and pass a stringent safety test. (FIG. 2A) $VRP_{RVF}$ (top) and RVFV (bottom) were used to infect VeroE6 monolayers. Over the course of 5 days (left to right), $VRP_{RVF}$ remain confined to the initially infected cells, while RVFV gradually spreads throughout the entire monolayer. Limit of detection: 1 fluorescent focus unit (FFU). (FIG. 2B) Survival curves of newborn suckling mice inoculated intracranially with $VRP_{RVF}$ or RVFV, or mock-inoculated.

FIGS. 3A-3D: Single dose immunization of replicating $VRP_{RVF}$ confers complete protection. (FIG. 3A) Survival curves of C57BL/6 mice in the $VRP_{RVF}$ dose titration experiment. Mice were immunized with $VRP_{RVF}$ and challenged 28 days later with virulent RVFV. (FIG. 3B) Survival curves of mice immunized with $VRP_{RVF}$ or nr-$VRP_{RVF}$ and challenged 28 days later with virulent RVFV. Survival curves are significantly different (p=0.005). (FIG. 3C) Total IgG titers of mice immunized with $VRP_{RVF}$ or nr-$VRP_{RVF}$ 28 days prior to serum collection. Limit of detection 1:100. (FIG. 3D) Virus neutralization titers of mice immunized with $VRP_{RVF}$ or nr-$VRP_{RVF}$ 28 days prior to serum collection. Limit of detection 1:10.

SEQUENCE LISTING

Figure 4A:
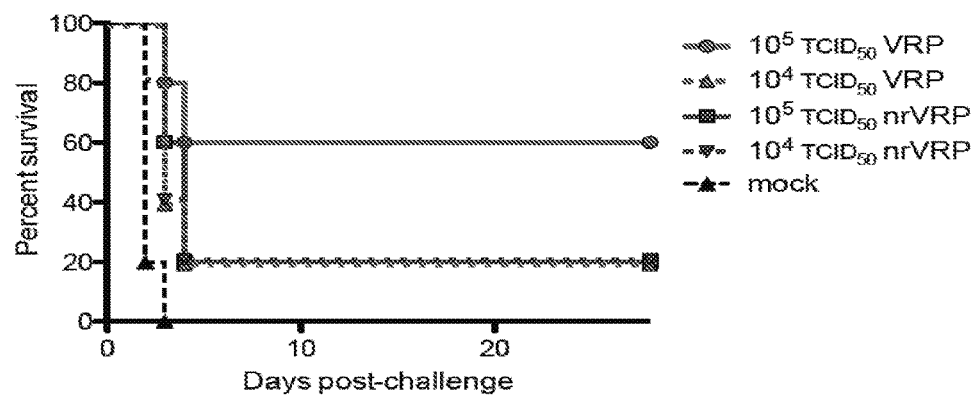
FIGS. 4A-4C: $VRP_{RVF}$ immunization is protective as early as 24 hours post-immunization. Shown are survival curves from early protection studies. C57BL/6 mice were immunized with $VRP_{RVF}$ or nr-$VRP_{RVF}$ and challenged with virulent virus (FIG. 4A) 24 hours, (FIG. 4B) 48 hours, or (FIG. 4C) 72 hours later. Survival curves were significantly different at 48 hours (p=0.008) and 72 hours (p=0.025).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Nov. 21, 2014, 15.1 KB, which is incorporated by reference herein. In the accompanying sequence listing:

SEQ ID NO: 1 is the nucleotide sequence of the antigenomic L segment of the RVFL plasmid.

SEQ ID NO: 2 is the nucleotide sequence of the antigenomic S segment of the RVFS-ΔNSs:GFP plasmid.

SEQ ID NO: 3 is the nucleotide sequence encoding RVFV Gn-Gc from the pC-GnGc expression vector.

DETAILED DESCRIPTION

I. Abbreviations

DIVA differentiation of naturally infected from vaccinated animals
DMEM Dulbecco's modified Eagle's medium
dpi days post-infection
ELISA enzyme-linked immunosorbent assay
FBS fetal bovine serum
FFU fluorescent focus unit
GFP green fluorescent protein
hpi hours post-infection
ic intracranial
IFA indirect fluorescent-antibody assay
IFN interferon
L large genome segment of RVFV
LD50 50% lethal dose
M medium genome segment of RVFV
NP nucleoprotein
nr-$VRP_{RVF}$ non-replicating $VRP_{RVF}$
NS non-structural
ORF open reading frame
PBS phosphate buffered saline
pfu plaque forming unit
PKR protein kinase R RVF Rift Valley fever
RVFV Rift Valley fever virus
S small genome segment of RVFV
sc subcutaneous
SM suckling mice
TCID 50% tissue culture infectious dose
VLP virus-like particle
$VNT_{100}$ 100% virus neutralization titer
VRP virus replicon particle
$VRP_{RVF}$ virus replicon particle of Rift Valley fever II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL. In some embodiments, $VRP_{RVF}$ functions as an adjuvant to enhance the immunogenicity of a heterologous vaccine.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Ambisense: Refers to a genome or genomic segments having both positive sense and negative sense portions. For example, the S segment of a *Phlebovirus*, such as Rift Valley fever virus, is ambisense, encoding nucleoprotein in the negative sense and the non-structural protein NSs in the positive sense.

Animal: Living multi-cellular vertebrate organisms, a category that includes, for example, mammals and bird. Mammals include, but are not limited to, humans, non-human primates, dogs, cats, horses, sheep, goats and cows. The term mammal includes both human and non-human mammals.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a RVF virus antigen.

Antigenomic: As used herein, "antigenomic" refers to a genomic segment of a *Phlebovirus* (such as RVF virus) in the orientation opposite to the viral genome. For example, Phleboviruses are negative-sense RNA viruses. Thus, "antigenomic" refers to the positive-sense orientation (or virus complementary sense), while "genomic" refers to the negative-sense orientation of a gene segment.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection.

Biological sample: A sample obtained from a subject (such as a human or veterinary subject). Biological samples include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) or other bodily fluid. Biological samples can also refer to cells or tissue samples, such as biopsy samples or tissue sections.

Cancer, tumor, neoplasia and malignancy: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In some cases, lymphomas are considered solid tumors.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Hepatitis delta virus ribozyme: A non-coding, catalytic RNA from the hepatitis delta virus. Ribozymes catalyze the hydrolysis of their own phosphodiester bonds or those of other RNA molecules.

Heterologous: As used herein a "heterologous protein" or "heterologous virus" is a protein or virus derived from a source other than Rift Valley fever virus.

Host cell: In the context of the present disclosure, a "host cell" is a cell of use with the RVF virus replicon system described herein. A suitable host cell is one that is capable of transfection with and expression of the plasmids of the RVF virus replicon system. In one embodiment, the host cell is a cell expressing the T7 polymerase, such as, but not limited to BSR-T7/5 cells (Buchholz et al., *J. Virol.* 73(1): 251-259, 1999).

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Immunize: To render a subject protected from an infectious disease, such as by vaccination.

Immunogen: A compound, composition, or substance which is capable, under appropriate conditions, of stimulating an immune response, such as the production of antibodies or a T-cell response in an animal, including compositions that are injected or absorbed into an animal. Accordingly, an "immunogenic protein" is a protein capable of stimulating an immune response in a subject, such as a human or animal subject. As used herein, an "immunogenic composition" is a composition comprising an immunogen.

Immunogenic composition: A composition useful for stimulating or eliciting a specific immune response (or immunogenic response) in a vertebrate. In some embodiments, the immunogenic composition includes $RVF_{VRP}$. In some embodiments, the immunogenic response is protective or provides protective immunity, in that it enables the subject to better resist infection with or disease progression from the pathogen against which the immunogenic composition is directed (e.g., Rift Valley fever virus). One specific example of a type of immunogenic composition is a vaccine.

Immunomodulatory protein: Any protein capable of modifying or regulating one or more functions of the immune system. Cytokines and chemokines are two exemplary types of immunomodulatory proteins. Specific immunomodulatory proteins include, but are not limited to, IFN-$\alpha$, IFN-$\beta$, IFN-$\gamma$ and TNF-$\alpha$.

Isolated: An "isolated" biological component (such as a nucleic acid, protein, virus or virus particle) has been substantially separated or purified away from other biological components (such as cell debris, or other proteins or nucleic acids). Biological components that have been "isolated" include those components purified by standard purification methods. The term also embraces recombinant nucleic acids, proteins, viruses or virus particles, as well as chemically synthesized nucleic acids or peptides.

Livestock: Domesticated animals reared in an agricultural setting as a source of food or to provide labor. The term "livestock" includes, but is not limited to, cattle, deer, donkeys, goats, horses, mules, rabbits and sheep.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more RVF virus replicon particles, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasmid: A circular nucleic acid molecule capable of autonomous replication in a host cell.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a T7 promoter (from bacteriophage T7).

Purified: The term "purified" does not require absolute purity; rather, it is intended as a relative term. Thus, for example, a purified peptide, protein, virus, virus particle or other active compound is one that is isolated in whole or in part from naturally associated proteins and other contaminants. In certain embodiments, the term "substantially purified" refers to a peptide, protein, virus, virus particle or other active compound that has been isolated from a cell, cell culture medium, or other crude preparation and subjected to fractionation to remove various components of the initial preparation, such as proteins, cellular debris, and other components.

Recombinant: A recombinant nucleic acid, protein, virus or virus particle is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In some embodiments, a recombinant RVF virus particle is generated using the VRP system described herein.

Reporter gene: A reporter gene is a gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell or tissue. Reporter genes include, for example, GFP (or eGFP) or other fluorescence genes, luciferase, β-galactosidase and alkaline phosphatase.

Reverse genetics: Refers to the process of introducing mutations (such as deletions, insertions or point mutations) into the genome of an organism or virus, such as to determine the phenotypic effect of the mutation or to engineer a specific mutation or alteration.

Rift Valley fever (RVF) virus (RVFV): A virus belonging to the family Bunyaviridae and genus *Phlebovirus*. RVF virus has a single-stranded, negative-sense genome composed of three genome segments, S, M and L. The S segment is an ambisense genome segment, meaning it encodes proteins in both the positive-sense and negative-sense orientations. The RVF virus genome encodes both structural and non-structural proteins. A "structural" protein is a protein found in the virus particle, whereas a "non-structural" protein is only expressed in a virus-infected cell. RVF virus structural proteins include nucleoprotein (NP or N, used interchangeably), two glycoproteins (Gn and Gc) and the viral RNA-dependent RNA polymerase (L protein). Non-structural RVF virus proteins include NSs, NSm and the NSm+Gn fusion protein. As used herein, a "full-length" RVF virus genome segment is one containing no deletions. Full-length genome segments can contain mutations or substitutions, but retain the same length as the wild-type virus. A "complete deletion" of an ORF of a RVF virus genome segment means either every nucleotide encoding the ORF is deleted from genome segment, or nearly every nucleotide encoding the ORF is deleted such that no proteins are translated from the ORF. Thus, a "complete deletion" includes genome segments retaining up to ten nucleotides encoding the ORF, such as one, two, three, four, five, six, seven, eight, nine or ten nucleotides. A number of RVF virus strains have been identified. In one embodiment described herein, the RVF virus strain is ZH501.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Pearson and Lipman, *Proc. Natl. Acad. Sci. U.S.A.* 85:2444, 1988; and Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals. Subjects include, but are not limited to veterinary subjects, including livestock such as cows, goats, sheep, and non-human primates, and human subjects.

Therapeutically effective amount or effective amount: A quantity of a specified agent sufficient to achieve a desired effect in a subject being treated with that agent. For example, this may be the amount of $VRP_{RVF}$ useful for eliciting an immune response in a subject and/or for preventing or inhibiting infection by RVF virus. Ideally, in the context of the present disclosure, a therapeutically effective amount of a $VRP_{RVF}$ (or an immunogenic composition thereof) is an amount sufficient to increase resistance to, prevent, ameliorate, and/or treat infection caused by RVF virus in a subject without causing a substantial cytotoxic effect in the subject. The effective amount of $VRP_{RVF}$ useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tumor antigen: An antigen that can stimulate tumor-specific T-cell immune responses. Exemplary tumor antigens include, but are not limited to, RAGE-1, tyrosinase, MAGE-1, MAGE-2, NY-ESO-1, Melan-A/MART-1, glycoprotein (gp) 75, gp100, beta-catenin, PRAME, MUM-1, WT-1, CEA, and PR-1. Additional tumor antigens are known in the art (for example see Novellino et al., *Cancer Immunol Immunother* 54(3):187-207, 2005).

Vaccine: A preparation of immunogenic material capable of stimulating an immune response, administered for the prevention, amelioration, or treatment of infectious or other types of disease. The immunogenic material may include attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Virus replicon particle (VRP): In the context of the present disclosure, a RVF virus replicon particle ($VRP_{RVF}$) is a viral particle that contains the RVF virus Gn, Gc, polymerase and nucleoproteins, and packaged within the particle are the RVF virus S and L genome segments. $VRP_{RVF}$ do not contain the RVF virus M segment or any nucleic acid molecule encoding the Gn and Gc glycoproteins. Thus, $VRP_{RVF}$ are capable of a single round of infection, including viral RNA expression and de novo viral protein synthesis, but cannot form new particles (due to the lack of Gn and Gc) and therefore cannot spread to neighboring cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Rift Valley fever virus (RVFV) causes outbreaks of severe disease in people and livestock throughout Africa and the Arabian Peninsula. The potential for RVFV introduction outside this endemic area highlights the need for fast-acting, safe, and efficacious vaccines. Disclosed herein is a robust system for the reverse genetics generation of a RVF virus replicon particle ($VRP_{RVF}$) vaccine candidate. Using a mouse model, it is shown that $VRP_{RVF}$ immunization provides the optimal balance of safety and single dose robust efficacy. $VRP_{RVF}$ can actively synthesize viral RNA and proteins, but lack structural glycoprotein genes, preventing spread within immunized individuals and reducing the risk of vaccine-induced pathogenicity.

VRP$_{RVF}$ were completely safe following intracranial inoculation of suckling mice, a stringent test of vaccine safety. Although highly attenuated, single dose VRP$_{RVF}$ subcutaneous immunization completely protected mice against a virulent RVFV challenge 100,000-fold greater than the LD$_{50}$. Robust protection from lethal challenge was observed by 24 hours post-vaccination, with 100% protection induced in as little as 96 hours. A single subcutaneous VRP$_{RVF}$ immunization initiated a systemic antiviral state followed by an enhanced adaptive response. The data provided in the present disclosure contrast sharply with the much reduced survivability and immune responses observed among animals immunized with non-replicating viral particles, indicating that replication, even confined to the initially infected cells, contributes substantially to protective efficacy at early and late time points post-immunization.

IV. Overview of Several Embodiments

Disclosed herein is the development and characterization of RVF virus replicon particles (VRP$_{RVF}$). VRP$_{RVF}$ are replication-competent but non-spreading virus particles. It is disclosed herein that VRP$_{RVF}$ are a safe and rapidly efficacious immunogenic composition (such as a vaccine) for protection against RVFV infection. In particular embodiments, VRP$_{RVF}$ contain full-gene deletions of the critical virulence factors NSs and NSm. As an additional safety measure, VRP$_{RVF}$ do not carry the genes for structural glycoproteins, and are therefore unable to produce new particles from infected cells, preventing spread within the immunized host and eliminating the risk of vaccine-induced pathogenicity.

The data disclosed herein demonstrate that VRP$_{RVF}$ immunization is both safe and efficacious against virulent RVFV challenge in a relevant animal model as early as 1 day after vaccination. Immunization with non-replicating VRP$_{RVF}$ (nr-VRP$_{RVF}$) resulted in significantly lower survival following RVFV challenge at both early and late time points. Relative to mock and nr-VRP$_{RVF}$-immunized animals, VRP$_{RVF}$ animals developed a stronger systemic antiviral and subsequent adaptive response following immunization, indicating that VRP$_{RVF}$ RNA and protein synthesis, even when confined to the initially infected cells, are critical for stimulating robust immunity and subsequent protection.

The RVF virus replicon particles (VRP$_{RVF}$) disclosed herein include a virus particle that contains a RVF virus L genome segment and a RVF virus S genome segment, but does not contain a RVF virus M genome segment (or any nucleic acid that encodes the RVF virus Gn and Gc proteins). The protein components of the VRP$_{RVF}$ include RVF virus Gn and Gc glycoproteins, polymerase protein and nucleoprotein.

Provided herein is a VRP$_{RVF}$, comprising (i) RVF virus Gn and Gc glycoproteins; (ii) RVF virus polymerase protein; (iii) RVF virus nucleoprotein; (iv) an RVF virus L genome segment; and (v) an RVF virus S genome segment, wherein the VRP$_{RVF}$ does not contain an RVF virus M segment or any nucleic acid molecule encoding the Gn and Gc glycoproteins.

In some embodiments, the S genome segment of the VRP$_{RVF}$ comprises a deletion, such as a complete deletion, of the NSs open reading frame (ORF). In particular examples, the NSs ORF is replaced by an ORF encoding a heterologous protein, such as a reporter gene ORF. Any gene that produces a protein with a functional readout can be used as the reporter gene. Reporter genes include, but are not limited to genes encoding fluorescent proteins, antibiotic resistance or enzymes (e.g., β-galactosidase or alkaline phosphatase). In some examples, the reporter gene is a GFP, such as enhanced GFP.

The VRP$_{RVF}$ disclosed herein can also be used as vaccine vectors to elicit an immune response against a heterologous protein. Thus, in some examples in which the NSs ORF is replaced by an ORF encoding a heterologous protein, the heterologous protein comprises an immunogenic protein from a heterologous virus (any virus other than Rift Valley fever virus), or from any other infectious organism against which an immune response is desired. In some cases, the heterologous protein is a vaccine or a component of a vaccine for an infectious organism, such as a bacterial or viral organism. In yet other examples, the heterologous protein is a tumor antigen.

In some embodiments, the VRP$_{RVF}$ does not contain an RVF virus NSm protein.

The RVF virus from which the RVF virus genome segments and proteins are derived can be any strain of RVF virus. Exemplary strains of RVF virus include, for example, ZH501, ZH548, MP-12, 35/74, SA75 and SPB 9800523. In specific examples, the RVF virus is RVF virus strain ZH501. In some examples, the RVF virus is not RVF virus strain 35/74.

The sequences of the S and L genome segments of the ZHSO1 strain are deposited under GenBank Accession No. DQ380149 and DQ375406, respectively. The nucleotide sequences of the S and L segments need not be 100% identical to a known RVF virus (such as ZHSO1) sequence. In some examples, the S and L segments are at least 80%, at least 85%, at least 90%, at least 95%, at least 96%, at least 97%, at least 98% or at least 99% identical to a known or disclosed RVF virus S or L segment, such as the S and L segments of ZHSO1. In some embodiments, the RVF virus S and L segments are at least 80%, at least 85%, at least 90%, at least 95%, at least 96%, at least 97%, at least 98% or at least 99% identical to an S or L segment disclosed in PCT Publication No. WO 2009/082647 or U.S. Patent Application Publication No. 2011-0123567, which are herein incorporated by reference in their entirety.

Further provided herein is a method of producing VRP$_{RVF}$, comprising (i) transfecting a host cell with a plasmid containing an antigenomic copy of an RVF virus L segment; a plasmid containing an antigenomic copy of an RVF virus S segment; and a plasmid encoding RVF virus Gn and Gc glycoproteins; and (ii) culturing the cells for a period of time sufficient to produce VRP$_{RVF}$. In some embodiments, the method further includes collecting the VRP$_{RVF}$ from the cell culture supernatant. In some examples, the method further includes isolating or purifying the VRP$_{RVF}$ from the cell culture supernatant.

In some embodiments of the method, the S genome segment comprises a deletion, such as a complete deletion, of the NSs ORF. In some examples, the NSs ORF is replaced by a reporter gene ORF. In particular examples, the reporter gene is a GFP, such as enhanced GFP. However, the reporter gene can be any gene that produces a protein with a functional readout, including genes that encode a fluorescent protein, antibiotic resistance or an enzyme.

In some embodiments, none of the plasmids used for producing the VRP$_{RVF}$ encode an RVF virus NSm protein.

In some embodiments, the plasmid containing an antigenomic copy of the S segment and the plasmid containing an antigenomic copy of the L segment further comprise a T7 promoter and a hepatitis delta virus ribozyme.

In some embodiments, the host cells express T7 polymerase. In particular examples, the host cells are BSR-T7/5 cells (Buchholz et al., *J. Virol.* 73(1):251-259, 1999).

The RVF virus genome segments and proteins used with the disclosed methods can be derived from any strain of RVF virus, including, but not limited to ZHSO1, ZH548, MP-12, 35/74, SA75 and SPB 9800523. In specific examples, the RVF virus is RVF virus strain ZHSO1. In some examples, the RVF virus is not RVF virus strain 35/74.

In specific examples, the plasmid containing an antigenomic copy of the L segment comprises a nucleotide sequence that is at least 85%, at least 90%, at least 95%, at least 96%, at least 97%, at least 98% or at least 99% identical to SEQ ID NO: 1. In one non-limiting embodiment, the nucleotide sequence of the plasmid containing an antigenomic copy of the L segment comprises SEQ ID NO: 1.

In other specific examples, the plasmid containing an antigenomic copy of the S segment comprises a nucleotide sequence that is at least 85%, at least 90%, at least 95%, at least 96%, at least 97%, at least 98% or at least 99% identical to SEQ ID NO: 2. In one non-limiting example, the nucleotide sequence of the plasmid containing an antigenomic copy of the S segment comprises SEQ ID NO: 2.

In other specific examples, the plasmid encoding RVF virus Gn and Gc glycoproteins comprises a nucleotide sequence that is at least 85%, at least 90%, at least 95%, at least 96%, at least 97%, at least 98% or at least 99% identical to SEQ ID NO: 3. In one non-limiting example, the nucleotide sequence of the plasmid encoding RVF virus Gn and Gc glycoproteins comprises SEQ ID NO: 3.

Also provided are $VRP_{RVF}$ produced according to a method disclosed herein.

Further provided are immunogenic compositions comprising the $VRP_{RVF}$ disclosed herein and a pharmaceutically acceptable carrier. Suitable pharmaceutical carriers are described herein and are well known in the art. The pharmaceutical carrier used depends on a variety of factors, including the route of administration. In one embodiment, the immunogenic composition further comprises an adjuvant. The adjuvant can be any substance that improves the immune response to the $VRP_{RVF}$.

Also provided is the use of $VRP_{RVF}$ as an adjuvant to enhance the immunogenicity of a heterologous protein, such as a heterologous vaccine. Thus, in some embodiments, the immunogenic compositions provided herein further include an immunogenic protein from a heterologous virus (any virus other than Rift Valley fever virus), or any other infectious microorganism.

Also provided is a method of eliciting an immune response against RVF virus in a subject. In some embodiments, the method includes administering to the subject an effective amount of $VRP_{RVF}$ or an immunogenic composition disclosed herein. Further provided is a method of immunizing a subject against RVF virus infection by administering to the subject an effective amount of $VRP_{RVF}$ or an immunogenic composition disclosed herein. In some embodiments, the subject is a human. In other embodiments, the subject is livestock, such as, for example, sheep or cattle.

In some embodiments of the methods, the $VRP_{RVF}$ or immunogenic composition is administered in a single dose. In another embodiment, the $VRP_{RVF}$ or immunogenic composition is administered in multiple doses, such as two, three or four doses. When administered in multiple doses, the time period between doses can vary. In some cases, the time period is days, weeks or months. The $VRP_{RVF}$ or immunogenic composition can be administered using any suitable route of administration. In some embodiments, the $VRP_{RVF}$ or immunogenic composition is administered intravenously, intramuscularly or subcutaneously.

A suitable does of $VRP_{RVF}$ (or immunogenic composition comprising the $VRP_{RVF}$) can be selected by a skilled practitioner. In some embodiments, the $VRP_{RVF}$ is administered at a dose of about $10^2$ to about $10^6$ $TCID_{50}$. In some examples, the $VRP_{RVF}$ is administered at a dose of about $10^4$ to about $10^5$ $TCID_{50}$. In particular examples, the $VRP_{RVF}$ is administered at a dose of about $10^2$, about $10^3$, about $10^4$, about $10^5$ or about $10^6$ $TCID_{50}$.

Further provided is a method of enhancing an immune response against an immunogenic protein, such as an immunogenic viral protein, in a subject by administering the immunogenic protein to the subject and further administering $VRP_{RVF}$.

Also provided is a method of eliciting an immune response against a heterologous protein in a subject, by administering to the subject $VRP_{RVF}$ in which the NSs ORF of the S genome segment is replaced by an ORF encoding the heterologous protein. In some embodiments, the heterologous protein is a protein from an infectious organism, such as a heterologous virus (any virus other than Rift Valley fever virus). In other embodiments, the heterologous protein is a tumor antigen.

Further provided is a method of treating cancer in a subject by selecting a subject with cancer and administering to the subject a therapeutically effective amount of the $VRP_{RVF}$ disclosed herein. For example, the $VRP_{RVF}$ can be administered systemically, such as intravenously, or can be administered directly into a tumor to promote destruction of tumor cells. In some embodiments, the NSs ORF of the S genome segment of the $VRP_{RVF}$ is replaced by an ORF encoding a tumor antigen, or other biologically active immunomodulatory protein, such as IFN-α, IFN-β, IFN-γ, TNF-α or the like. In some embodiments, the subject is further administered an anti-cancer agent and/or other therapeutic treatment for cancer, such as surgical removal of the tumor of a portion thereof. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and antibodies that specifically target cancer cells.

Also provided is a method of differentiating a subject administered the $VRP_{RVF}$ disclosed herein from a subject naturally infected with RVF virus. In some embodiments, the method includes obtaining a biological sample from the subject; and detecting the presence or absence of anti-nucleoprotein antibodies and either anti-NSm or anti-NSs antibodies in the sample. The presence of anti-nucleoprotein and anti-NSm and/or anti-NSs antibodies in the sample indicates that the subject was naturally infected with RVF virus. The presence of anti-nucleoprotein antibodies and the absence of anti-NSm and/or anti-NSs antibodies in the sample indicates that the subject was administered the $VRP_{RVF}$.

In some embodiments, the biological sample is a bodily fluid sample. In particular examples, the bodily fluid sample is a blood or serum sample.

In some embodiments of the differential diagnosis method, the subject is human. In other embodiments, the subject is livestock.

V. Administration of Rift Valley Fever Virus Replicon Particles (VRP$_{RFV}$)

VRP$_{RFV}$, or immunogenic compositions thereof, can be administered to a subject by any of the routes normally used for introducing virus or virus particles into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Immunogenic compositions are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent RVF virus infection. The dose required will vary from subject to subject depending on the species, age, weight and general condition of the subject, the severity of the infection being treated, the particular immunogenic composition being used and its mode of administration. An appropriate dose can be determined by one of ordinary skill in the art using only routine experimentation.

Provided herein are pharmaceutical compositions (also referred to as immunogenic compositions) which include a therapeutically effective amount of the VRP$_{RFV}$ alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The VRP$_{RFV}$ described herein can be administered alone or in combination with other therapeutic agents to enhance antigenicity. For example, the VRP$_{RFV}$ can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

VI. Use of VRP$_{RVF}$ and Immunogenic Compositions Thereof

The VRP$_{RVF}$ and immunogenic compositions comprising VRP$_{RVF}$ disclosed herein can be used, for example, to elicit an immune response in a subject or to immunize a subject against RVF virus. In some embodiments, the immunogenic compositions disclosed herein are used as vaccines to prevent or inhibit infection by RVF virus. The disclosed VRP$_{RVF}$ and immunogenic compositions can be used for example, to prevent or inhibit RVF infection in humans or in livestock, such as cattle, sheep or goats.

The VRP$_{RVF}$ and immunogenic compositions disclosed herein can be targeted towards veterinary medical use, and thus indirectly prevent human RVF disease; however, the candidate vaccines can also provide effective prophylactic protection for humans, such as those in high risk occupational settings, or in recognized risk groups following natural or intentional introduction of RVF virus into previously unaffected areas.

Efforts to prevent RVF virus infection via vaccination began shortly after the first isolation of the virus in 1931 (Findlay and Daubney, *Lancet* ii:1350-1351, 1931). These earliest vaccines (MacKenzie, *J. Pathol. Bacteriol.* 40:65-73, 1935) and several that followed, including the currently available TSI-GSD-200 preparation, relied on formalin inactivation of live wild-type virus (Pittman et al., *Vaccine* 18:181-189, 1999; Randall et al., *J. Immunol.* 89:660-671, 1962). While capable of eliciting protective immune responses among livestock and humans, these inactivated vaccines typically require a series of 2 or 3 initial inoculations, followed by regular booster vaccinations to achieve and maintain protection (Pittman et al., *Vaccine* 18:181-189, 1999; Swanepoel et al., "Rift Valley fever" in Infectious Diseases of livestock with special reference to South Africa, pages 688-717, Oxford university Press, Cape Town). However, multiple dosing and annual vaccination regimens are logistically difficult to implement and expensive to maintain, and thus are of limited practical value in resource-poor settings, especially in regard to control of RVF virus infection in livestock in enzootic settings. In addition, there have been problems in the past with quality control and "inactivated" vaccines causing disease.

In an effort to eliminate the necessity of booster inoculations, several live-attenuated vaccine candidates were developed for RVF virus with some, such as the Smithburn neurotropic strain, being employed in Africa. These vaccine candidates have relied upon the random introduction of attenuating mutations via serial passage in suckling mouse brain or tissue culture, in vitro passage in the presence of chemical mutagens, such as 5-flurouracil, or as naturally occurring virus isolates (such as the Smithburn neurotropic strain, the Kenyan-IB8 strains, MP-12, or the Clone 13 isolate) (Caplen et al., *J. Gen. Virol.* 66:2271-2277, 1985; Coackley, *J. Pathol. Bacteriol.* 89:123-131, 1965; Moussa et al., *Am. J. Trop. Med. Hyg.* 35:660-662, 1986; Muller et al., *Am J. Trop. Med. Hyg.* 53:405-411, 1995; Rossi and Turell, *J. Gen. Virol.* 69:817-823, 1988; Smithburn, *Br. J. Exp. Pathol.* 30:1-16, 1949).

Due to the technical limitations of these procedures, and the lack of complete genome sequence for many of the historically derived RVF virus vaccines, the exact underlying molecular mechanisms of attenuation for many of these live-attenuated RVF virus vaccines is either unknown (Smithburn neurotropic strain or Kenyan-IB8) or reliant on the combinatorial effects of multiple nucleotide or amino acid substitutions (MP-12) (Saluzzo and Smith, *Vaccine* 8:369-375, 1990; Takehara et al., *Virology* 169:452-457, 1989). Experimental and field experience with existing live-attenuated RVF virus vaccines demonstrated that in certain instances these vaccines retain the ability to cause teratogenic effects, abortion, and neural pathology in livestock or animal models. Thus, widespread use of these live-attenuated vaccines is problematic, especially in non-endemic areas, or during inter-epizootic/epidemic periods (Hunter et al., *Onderstepoort J. Vet. Res.* 69:95-98, 2002; Morrill et al., *Am. J. Vet. Res.* 58:1104-1109, 1997; Morrill et al., *Am. J. Vet. Res.* 58:1110-1114, 1997; Morrill and Peters, *Vaccine* 21:2994-3002, 2003).

Several distinct disadvantages exist among live attenuated RNA virus vaccines prepared by the traditional techniques discussed above. Live-attenuated vaccines reliant on single or multiple nucleotide substitutions are at increased risk for reversion to virulent phenotypes due to the inherently high rate of viral RNA polymerase errors. The loss of attenuation via this mechanism among livestock and human live vaccines has been documented (Berkhout et al., *J. Virol.* 73:1138-1145, 1999; Catelli et al., Vaccine 24:6476-6482, 2006; Halstead et al., *Am. J. Trop. Med. Hyg.* 33:672-678, 1984; Hopkins and Yoder, *Avian Dis.* 30:221-223, 1986; Rahimi et al., *J. Clin. Virol.* 39:304-307, 2007).

The potential for a similar reversion event among live RVF virus vaccines dependent on attenuating nucleotide mutation was illustrated by a genomic analyses of RVF virus that revealed an overall molecular evolution rate ($\sim 2.5 \times 10^{-4}$ nucleotide substitutions/site/year) similar to other single-stranded RNA viruses (Bird et al., *J. Virol.* 81:2805-2816, 2007). Due to error-prone polymerases, live-attenuated RNA virus vaccines prepared by multiple serial passage techniques involved in virus attenuation inherently consist of a complex mixture of genomic micro-variants. In contrast, the origin of reverse genetics derived virus vaccine candidates (including the $VRP_{RVF}$ disclosed herein) is advantageous in that vaccine stocks can be generated directly from precisely defined DNA plasmids. This approach allows for the simple production of virus vaccines following good manufacturing processes (GMP) with higher levels of genetic homogeneity.

Another significant drawback of all previously generated live-attenuated RVF virus vaccines is that they do not allow for differentiation of naturally infected from vaccinated animals (DIVA). This ability is important to augment efforts to contain an accidental or intentional release of wild-type RVF virus in previously unaffected areas (Henderson, *Biologicals* 33:203-209, 2005). As a high consequence pathogen, RVF virus has been classified as a category A Select Agent as defined by the United States Department of Health and Human Services and the United States Department of Agriculture (USDA), and is listed as a high consequence agent with potential for international spread (List A) by the Office International des Epizooties (OIE) (Le May et al., *Cell* 116:541-550, 2004) of the World Organization for Animal Health (WOAH), thus greatly increasing the consequences for international livestock trade following the introduction of RVF virus into previously unaffected countries or epizootics in enzootic areas (USDA, 7 CFR Part 331 and 9 CFR Part 121, Federal Register RIN 0579-AB47:13241-13292, 2005). Currently, OIE regulations require surveillance and absence of RVF virus activity for 2 years following an outbreak before resumption of disease free status and the subsequent easing of import/export trade restrictions (International Office of Epizootics, Terrestrial Animal Health Code, XI:2.2.14.1, 2007). The use of any current commercially available livestock vaccines does not permit the differentiation of vaccinated from naturally infected livestock, thus contraindicating the use of prophylactic vaccination in countries wishing to retain disease free status, or in those with ongoing/endemic RVF virus activity.

The $VRP_{RVF}$ disclosed herein do contain or encode the NSs or NSm proteins, which allows for the serologic differentiation of naturally infected and vaccinated animals by presence/absence of anti-RVF NP/anti-RVF NSs antibodies.

Thus, the $VRP_{RVF}$ disclosed herein have several distinct advantages over prior RVF virus vaccines—they exhibit rapid and robust efficacy, enhanced safety, are incapable of reverting to a virulent virus, and infection by $VRP_{RVF}$ can be distinguished from natural RVF virus infection (DIVA).

The $VRP_{RVF}$ disclosed herein can also be used as adjuvants to enhance the immunogenicity of another vaccine. As described herein, $VRP_{RVF}$ elicit rapid and robust immunogenicity, indicating these particles are capable of functioning as a strong adjuvant.

$VRP_{RVF}$ can further be used as vaccine vectors to deliver a heterologous protein as a means of eliciting an immune response against the heterologous protein. The data disclosed herein demonstrate that replacement of the NSs ORF with GFP resulted in robust GFP expression within VRP-infected cells. It is further disclosed herein that $VRP_{RVF}$ infection in vivo resulted in a strong innate immune response.

Thus, provided herein is a method of eliciting an immune response against a heterologous protein in a subject by administering to the subject $VRP_{RVF}$ in which the NSs ORF of the S genome segment is replaced by an ORF encoding the heterologous protein. In some embodiments, the heterologous protein is a protein from an infectious organism, such as a heterologous virus (any virus other than Rift Valley fever virus). In other embodiments, the heterologous protein is a tumor antigen.

In particular embodiments, provided herein is a method of eliciting an immune response against a heterologous viral protein in a subject by administering to the subject $VRP_{RVF}$ in which the NSs ORF of the S genome segment is replaced by an ORF encoding a heterologous viral protein. In other particular embodiments, provided herein is a method of eliciting an immune response against a tumor antigen by administering to the subject $VRP_{RVF}$ in which the NSs ORF of the S genome segment is replaced by an ORF encoding a tumor antigen.

The VRPRVF disclosed herein can also be used as anticancer agents to promote destruction of tumor cells. Thus, in some embodiments, provided is a method of treating cancer in a subject by selecting a subject with cancer and administering to the subject a therapeutically effective amount of the $VRP_{RVF}$ disclosed herein. In some examples, the $VRP_{RVF}$ are administered systemically, such as intravenously, for example by infusion. Systemic administration is particularly useful for metastatic cancer. In other examples, the $VRP_{RVF}$ are administered directly into a tumor. In some embodiments, the NSs ORF of the S genome segment of the $VRP_{RVF}$ is replaced by an ORF encoding a tumor antigen.

In some embodiments, the subject is further administered a second anti-cancer agent and/or other therapeutic treatment for cancer, such as surgical removal of the tumor of a portion thereof. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and antibodies that specifically target cancer cells.

The following examples are provided to illustrate certain particular features and/or embodiments. These examples should not be construed to limit the disclosure to the particular features or embodiments described.

EXAMPLES

Example 1: Materials and Methods

This example describes the experimental procedures for the studies described in Example 2.
Cell Culture and Biosafety BSR-T7/5 and VeroE6 cells were propagated in Dulbecco's modified Eagle's medium (DMEM) supplemented with 5% fetal bovine serum (FBS) and penicillin-streptomycin (Invitrogen). BSR-T7/5 cells were maintained under selection with G418 every other passage (1 mg/mL; Geneticin; Invitrogen). All animals were housed within BSL-4 or BSL-3+ laboratories in microisolator pans in HEPA filtration racks, following standard barrier techniques.
Animal Immunization and Infection For the suckling mouse safety test, 2-day-old CD-1 (ICR) mice (Charles River Laboratories) were inoculated intracranially (ic) with $1.0 \times 10^4$ 50% tissue culture infective dose ($TCID_{50}$) $VRP_{RVF}$, or with $1.0 \times 10^4$ plaque forming units (pfu) of recombinant RVFV ZHSO1 (RVFV) in a total volume of 10 μL DMEM. Mock-immunized mice were inoculated with 10 μL DMEM ic. Mice were evaluated daily for 28 days post-immunization (dpi), and animals were euthanized if found in distress or moribund.

Four experiments used 10-12-week-old female C57BL/6 mice (Jackson Laboratory): (i) $VRP_{RVF}$ dose titration for minimum effective immunization dose; (ii) vaccine efficacy and immunogenicity of $VRP_{RVF}$ and nr-$VRP_{RVF}$ at 28 dpi; (iii) $VRP_{RVF}$ and nr-$VRP_{RVF}$ efficacy at 1-4 dpi; and (iv) systemic immune responses of $VRP_{RVF}$ and nr-$VRP_{RVF}$ immunized mice during the first 24 hours post-immunization (hpi). In these experiments, mice were immunized subcutaneously (sc) with $VRP_{RVF}$ or nr-$VRP_{RVF}$ in doses ranging from 10 to $1.0 \times 10^5$ $TCID_{50}$ prepared in a total volume of 100 μL DMEM. Mock immunized controls were inoculated with 100 μL DMEM. Mice were challenged sc with $1.0 \times 10^5$ pfu RVFV in 100 μL DMEM. Animals were evaluated at least once daily for 28 dpi. All animals were euthanized according to a pre-determined clinical illness scoring algorithm or if found in acute distress or moribund.
Plasmid Construction Construction of the full length RVFL, RVFM, and RVFS plasmids, and the RVFM-ΔNSm and RVFS-ΔNSs:GFP plasmids has been described previously (Bird et al., *Virology* 362:10-15, 2007). The plasmids contain the viral antigenome flanked by the T7 promoter (5' terminus), and the hepatitis Δ virus ribozyme and T7 polymerase terminator motifs (3' terminus). For this study, the open reading frame (ORF) encoding the RVFV glycoproteins, Gn and Gc, was amplified by PCR (nt 408-3614, as in GenBank Accession No. DQ380200) and cloned into the pCAGGS expression plasmid (Niwa et al., *Gene* 108:193-199, 1991) using standard cloning techniques (pC-GnGc). Two silent mutations were introduced into the Gn/Gc ORF used for $VRP_{RVF}$ generation to differentiate this ORF from that of wild-type virus.
$VRP_{RVF}$ and RVFV Production $VRP_{RVF}$, wild-type RVFV, and RVFV-ΔNSm/ΔNSs:GFP viruses were produced using an established 3-plasmid RVFV reverse genetics system. As described previously, rescue of recombinant wild-type RVFV ZHSO1 (RVFV) was accomplished using RVFL, RVFM, and RVFS plasmids (Bird et al., *Virology* 362:10-15, 2007), and RVFV-ΔNSm/ΔNSs:GFP was rescued using RVFL, RVFM-ΔNSm, and RVFS-ΔNSs:GFP plasmids (Bird et al., *J. Virol.* 82:2681-2691, 2008; U.S. Patent Application Publication No. 2011-0123567). $VRP_{RVF}$ were rescued similarly using RVFL, RVFS-ΔNSs:GFP, and pC-GnGc plasmids. Briefly, BSR-T7/5 cells were seeded in a 6-well plate format. Cells were transfected at approximately 75% confluency with 1 μg of each plasmid and LT1 transfection reagent (Minis) in a ratio of 1 μg:4 μl LT1. Rescue of $VRP_{RVF}$ resulted only from cells transfected with all 3 plasmids. Supernatants were harvested at 4 days post-transfection, subjected to low-speed centrifugation to clear cellular debris, and stored at −80° C. Non-replicating $VRP_{RVF}$ (nr-$VRP_{RVF}$) were generated by exposing $VRP_{RVF}$ to γ-irradiation ($5 \times 10^6$ rads), following a standard CDC protocol for removing antigen preparations from BSL-4 containment for diagnostic testing in a BSL-2 laboratory. This protocol completely abolishes viral (or $VRP_{RVF}$) replication while preserving the antigenicity of the sample.
$VRP_{RVF}$ Titration and One-Step Growth Curve To determine $VRP_{RVF}$ titer and production kinetics, BSR-T7/5 transfection supernatants were harvested from individual wells of a 6-well plate 1, 2, 3, 4, or 5 days post-transfection, clarified by low-speed centrifugation and frozen at −80° C. $VRP_{RVF}$ titers were determined as $TCID_{50}$ on VeroE6 cells. Initial titration of $VRP_{RVF}$-infected cells was based on eGFP fluorescence and confirmed by indirect fluorescent-antibody assay (IFA) using an anti-RVF primary antibody.

Total Anti-RVFV IgG Enzyme-Linked Immunosorbent Assay (ELISA)

Total anti-RVFV IgG ELISA testing was completed using whole cell lysates from RVFV infected Vero E6 cells or uninfected Vero E6 cells at 1:2000 following standard CDC Viral Special Pathogens Branch diagnostic protocols as described previously (Bird et al., *J. Virol.* 85:12901-12909, 2011).

Virus Neutralization Titers ($VNT_{100}$)

RVFV stock was diluted to 3000 $TCID_{50}$ in 50 µL DMEM without FBS. Sera from $VRP_{RVF}$, nr-$VRP_{RVF}$, and mock-immunized mice were heat-inactivated at 56° C. for 30 minutes. In a 96-well plate, 1:10, 1:20, 1:40, 1:80, 1:160, 1:320, and 1:640 serum dilutions were made in 50 µL DMEM. An equal volume of diluted RVFV was added to diluted sera and incubated for 1 hour at 37° C. A suspension of approximately $3 \times 10^4$ VeroE6 cells was added to each well, and the plates were incubated for 36 hours before formalin fixation. Cells were visualized with an IFA using an anti-RVFV primary antibody. $VNT_{100}$ were defined as the highest dilution that permitted complete (100%) neutralization of virus input.

Electron Microscopy $VRP_{RVF}$ and RVFV samples from the supernatants of transfected BSRT7/5 cells were taken 3 days post-transfection, fixed with 4% paraformaldehyde, and inactivated by γ-irradiation for removal from containment laboratory. Each sample was incubated overnight on 400 mesh nickel grids at 4° C. Grids were rinsed once and stained with 5% ammonium molybdate and 0.1% trehalose. Specimens were viewed at 120 kV on a Tecnai FEI electron microscope (FEI).

In Vivo Safety Assessment

A total of 30 2-day-old suckling mice (SM) were inoculated with $1.0 \times 10^4$ $TCID_{50}$ $VRP_{RVF}$. 10 SM were inoculated with $1.0 \times 10^4$ pfu RVFV (positive control), and 20 SM were inoculated with 10 µL DMEM (negative control).

$VRP_{RVF}$ Dose Titration

A total of 25 mice were immunized sc in groups of 5 with $1.0 \times 10^5$, $1.0 \times 10^4$, $1.0 \times 10^3$, $1.0 \times 10^2$, or 10 $TCID_{50}$ $VRP_{RVF}$, and 5 mice were mock immunized with DMEM. Mice were evaluated once daily for clinical signs. At 28 dpi, all mice were challenged with a lethal dose of $1.0 \times 10^5$ pfu RVFV sc.

Efficacy and Immunogenicity of $VRP_{RVF}$ and Nr-$VRP_{RVF}$ at 28 Dpi

Mice were immunized sc in 5 groups: (i) $1.0 \times 10^5$ $TCID_{50}$ $VRP_{RVF}$ (n=10); (ii) $1.0 \times 10^4$ $TCID_{50}$ $VRP_{RVF}$ (n=13); (iii) $1.0 \times 10^5$ $TCID_{50}$ nr-$VRP_{RVF}$ (n=10); (iv) $1.0 \times 10^4$ $TCID_{50}$ nr-$VRP_{RVF}$ (n=13); and (v) sham-immunized with DMEM. At 28 dpi, 5 mice from each group were challenged with a lethal dose of $1.0 \times 10^5$ pfu RVFV sc and evaluated daily for 28 days. The remaining mice in each group were anesthetized with isoflurane for serum collection for determination of total anti-RVFV IgG and neutralizing antibody titers.

$VRP_{RVF}$ and nr-$VRP_{RVF}$ Efficacy at Early Time Points

A total of 100 mice were immunized sc in 5 groups of 20: (i) $1.0 \times 10^5$ $TCID_{50}$ $VRP_{RVF}$ (ii) $1.0 \times 10^4$ $TCID_{50}$ $VRP_{RVF}$ (iii) $1.0 \times 10^5$ $TCID_{50}$ nr-$VRP_{RVF}$ (iv) $1.0 \times 10^4$ $TCID_{50}$ nr-$VRP_{RVF}$; and (v) mock-immunized with DMEM. On each of days 1, 2, 3, and 4, a subset of 5 mice from each group (25 total) were challenged sc with $1.0 \times 10^5$ pfu virulent RVFV and evaluated twice daily for clinical signs of disease.

Comparison of Early Immune Response of $VRP_{RVF}$ and nr-$VRP_{RVF}$ Immunized Mice A total of 24 mice were immunized sc in 3 groups of 8: (i) $1.0 \times 10^4$ $TCID_{50}$ $VRP_{RVF}$; (ii) $1.0 \times 10^4$ $TCID_{50}$ nr-$VRP_{RVF}$; or (iii) mock-immunized with 100 µL DMEM. At 12 and 24 hpi, 4 mice from each group were anesthetized with isoflurane and perfused with PBS. Approximately 100 µg samples from the perfused liver and brain were placed in RNAlater™ (Ambion Inc.) and frozen at −80° C. until used for RNA extraction.

RNA Extraction

To extract mRNA from tissues, tissue samples were removed from RNAlater™, and placed in 1 mL of Tripure™ isolation reagent (Roche Applied Science). RNA was extracted using the Qiagen RNeasy™ mini kit per manufacturer's instructions, including the RNase-free DNase step (Qiagen).

Antiviral Assays

Antiviral Response quantitative PCR arrays (SABiosciences) were used to determine up- or down-regulation of a select panel of 84 antiviral genes in mice immunized with $VRP_{RVF}$ or nr-$VRP_{RVF}$, relative to mock immunized mice. Assays were run on liver and brain samples from 3 $VRP_{RVF}$-immunized mice, 3 nr-$VRP_{RVF}$-immunized mice, and 3 mock-immunized mice at each time point. For each sample, cDNA was synthesized from 0.8-1.0 µg of RNA using the $RT^2$ first strand kit (SABioscience). Arrays were run on an ABI 7500 using $RT^2$ SYBR™ Green/ROX PCR master mix according to the manufacturer's instructions (SABioscience).

Statistical Analyses

For efficacy experiments, the Gehan-Breslow-Wilcoxon test was used to determine whether survival curves were significantly different (GraphPad Prism, GraphPad Software Inc.). A student's t-test was used to determine statistical significance of $VNT_{100}$ and IgG titers.

In the antiviral array analysis, the mean value of each gene was calculated for each set of replicate tissue samples using the $\Delta\Delta C_t$ method, and normalized to the average of 5 housekeeping genes (Gus-β, Hprt, HSP-90AB1, GAPDH, and β-actin). The p values were calculated based on a student's t-test of the replicate $2^{-\Delta Ct}$ values (SABioscience) for each gene in the $VRP_{RVF}$ and nr-$VRP_{RVF}$ groups.

Example 2: Single Dose Immunization with Virus Replicon Particles Confers Rapid Robust Protection Against Rift Valley Fever Virus Challenge This example describes the finding that a single dose of $VRP_{RVF}$ provides complete protection against RVFV challenge, and that complete protection is conferred within 96 hours of vaccination.

$VRP_{RVF}$ High Yield Production and Growth Kinetics

Figures 1A, 1B:
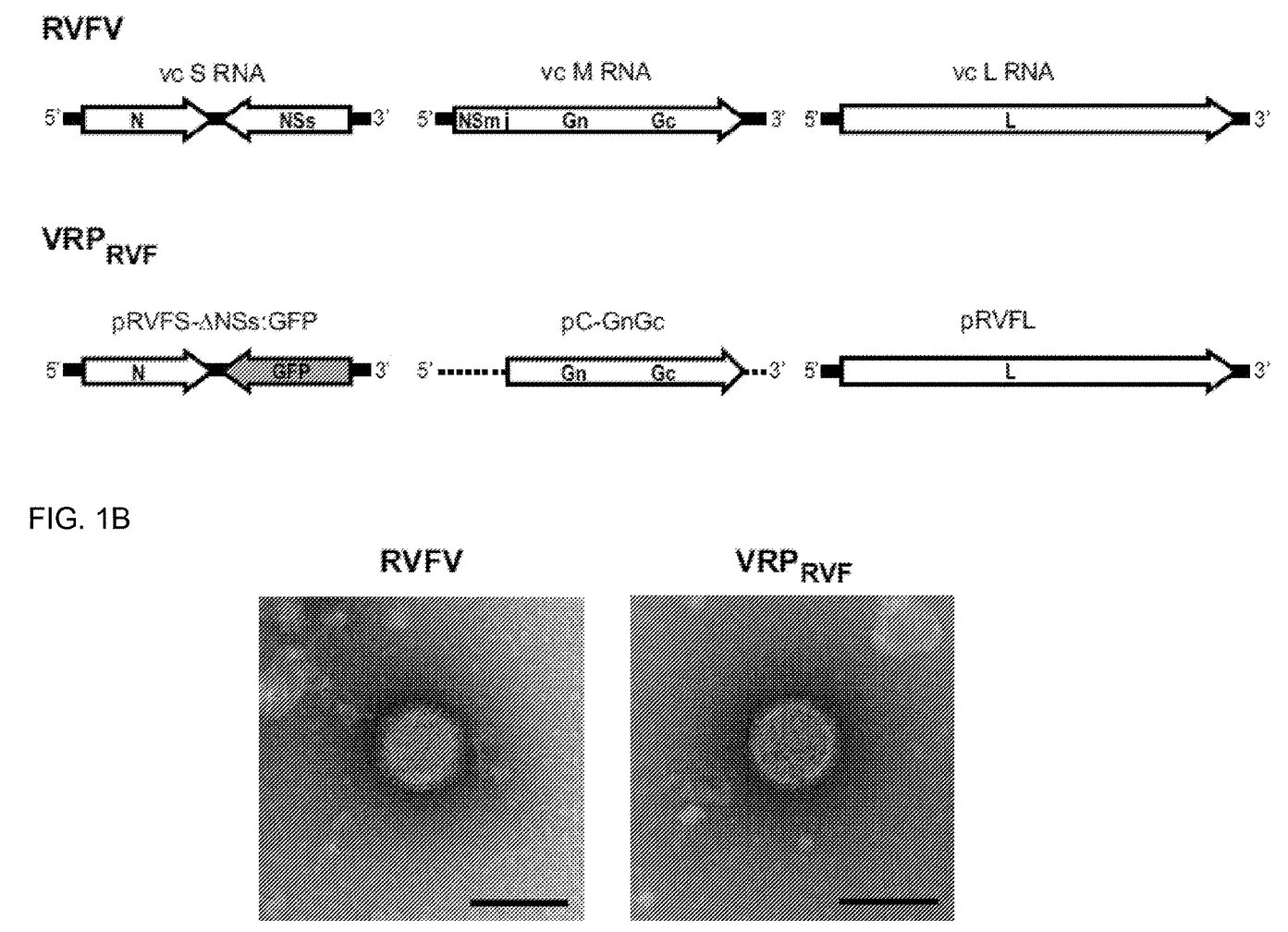

Efficient $VRP_{RVF}$ production was accomplished with an established RVFV reverse genetics system and simultaneous transfection of 3 plasmids: RVFL (wild-type L segment; SEQ ID NO: 1), RVFS-ΔNSs:GFP (S segment with GFP replacing NSs; SEQ ID NO: 2), and pC-GnGc (expression vector carrying glycoprotein genes; SEQ ID NO: 3) (FIG. 1A). $VRP_{RVF}$ were produced from cells transfected with all 3 plasmids and rescued directly from BSR-T7/5 transfection media. Total $VRP_{RVF}$ production increased from 1 day through 4 days after transfection, and declined at 5 days. In several independent experimental replicates, $VRP_{RVF}$ were rescued with 100% efficiency with titers ranging from $1.0 \times 10^6$ to $5.0 \times 10^7$ $TCID_{50}$/mL (average titer=$1.2 \times 10^7$ $TCID_{50}$/mL). Recombinant wild-type RVFV ZHSO1 and RVFV-ΔNSm/ΔNSs:GFP, a GFP-expressing virus with full-gene deletions of NSs and NSm, were also successfully rescued as described previously (Bird et al., *Virology* 362: 10-15, 2007; U.S. Patent Application Publication No. 2011-0123567).

VRP$_{RVF}$ are Morphologically Indistinguishable from RVFV

To compare the morphology of replicon particles to virus particles, VRP$_{RVF}$ and RVFV particles were harvested from BSRT7/5 cells at 3 days after transfection for electron microscopy analysis. VRP$_{RVF}$ and classic RVFV particles ranged in size between 80-100 nm, were round to slightly pleiomorphic, and indistinguishable from one another (FIG. 1B).

VRP$_{RVF}$ do not Spread Beyond Initially Infected Cells

To illustrate that VRP$_{RVF}$ only undergo one round of infection, VeroE6 cell monolayers were infected with VRP$_{RVF}$ and RVFV-ΔNSm/ΔNSs:GFP, and monitored daily for 5 days. While RVFV spreads rapidly throughout the cell monolayer, the VRP$_{RVF}$ do not spread beyond the initially infected cells (FIG. 2A).

VRP$_{RVF}$ is Completely Safe in Suckling Mouse Infections

In a stringent vaccine safety test, newborn (2-day-old) suckling mice were inoculated is with $1.0 \times 10^4$ TCID$_{50}$ VRP$_{RvF}$, $1.0 \times 10^4$ pfu RVFV, or 10 μL DMEM. All RVFV-inoculated mice died 2 days after infection. All mice inoculated with VRP$_{RVF}$ or DMEM survived with no indication of clinical signs (FIG. 2B).

Figures 3A, 3B, 3C, 3D:
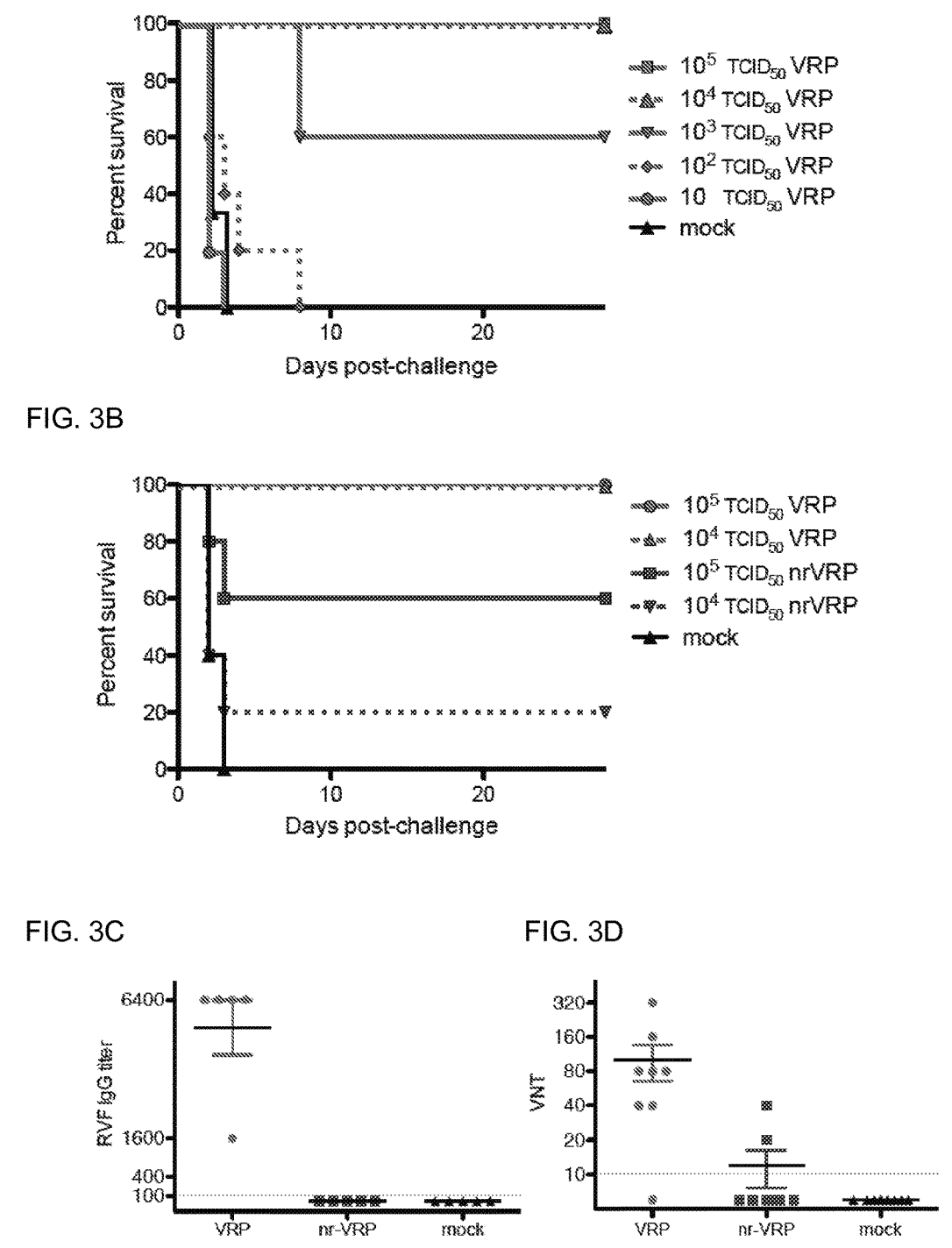

Single Dose Immunization with VRP$_{RVF}$ is Completely Protective from Virulent Virus Challenge A dose titration study was conducted to determine the minimum VRP$_{RVF}$ immunization that confers protection from virulent virus challenge. Mice were immunized sc in groups of 5 with 10, $1.0 \times 10^2$, $1.0 \times 10^3$, $1.0 \times 10^4$, or $1.0 \times 10^5$ TCID$_{50}$ VRP$_{RVF}$, or mock-immunized with DMEM, and challenged sc with $1.0 \times 10^5$ pfu RVFV. Previous experiments indicated the 50% lethal dose (LD$_{50}$) of RVFV ZHSO1 in adult C57BL/6 mice is less than 1 pfu; therefore the virus challenge for all experiments in this study was 100,000-fold higher than the LD$_{50}$. Results showed a dose-dependent effect on survival. A single dose immunization with $1.0 \times 10^5$ or $1.0 \times 10^4$ TCID$_{50}$ VRP$_{RVF}$ conferred 100% protection against virus challenge, whereas $1.0 \times 10^3$ TCID$_{50}$ VRP$_{RVF}$ protected 60% of mice. Although there were no survivors in groups given lower VRP$_{RVF}$ doses, mortality was delayed in mice receiving $1.0 \times 10^2$ TCID$_{50}$ (FIG. 3A).

Active Replication of VRP$_{RVF}$ is Important for Complete Protection

To evaluate the relative importance of VRP$_{RVF}$ replication for vaccine efficacy, mice were immunized with replicating VRP$_{RVF}$ or non-replicating (nr) VRP$_{RVF}$ at doses of $1.0 \times 10^5$ or $1.0 \times 10^4$ TCID$_{50}$, or mock-immunized with DMEM, and were challenged with $1.0 \times 10^5$ pfu virulent RVFV. As seen in the earlier experiment, all mice immunized with a single dose of $1.0 \times 10^5$ or $1.0 \times 10^4$ TCID$_{50}$ VRP$_{RVF}$ survived lethal virus challenge with no clinical signs. In contrast, only 60% and 20% of the mice immunized with $1.0 \times 10^5$ or $1.0 \times 10^4$ TCID$_{50}$ nr-VRP$_{RVF}$, respectively, survived challenge (FIG. 3B).

Replicating VRP$_{RVF}$ Induce IgG Response by 28 Dpi

The IgG antibody responses of mice immunized with $1.0 \times 10^5$ TCID$_{50}$ VRP$_{RvF}$, $1.0 \times 10^5$ TCID$_{50}$ nr-VRP$_{RVF}$, or DMEM were evaluated 28 dpi. Mice immunized with VRP$_{RVF}$ had total anti-RVF IgG titers ranging from 1600 (1/5) to 6400 (4/5). None of the mice immunized with nr-VRP$_{RVF}$ had detectable IgG response (limit of detection 1:100; FIG. 3C).

VRP$_{RVF}$ Induce a Significantly Stronger Neutralizing Antibody Response than Nr-VRP$_{RVF}$ Also at 28 dpi, the neutralizing antibody response of mice immunized with $1.0 \times 10^4$ TCID$_{50}$ VRP$_{RVF}$ or nr-VRP$_{RVF}$ was assessed. Seven of the 8 VRP$_{RVF}$-immunized mice had detectable levels of neutralizing antibodies, as compared with 2 of the 8 nr-VRP$_{RVF}$-immunized mice. VNT$_{100}$ were significantly higher in VRP$_{RVF}$-immunized mice than nr-VRP$_{RVF}$-immunized mice (p<0.05; FIG. 3D).

Figure 4B:
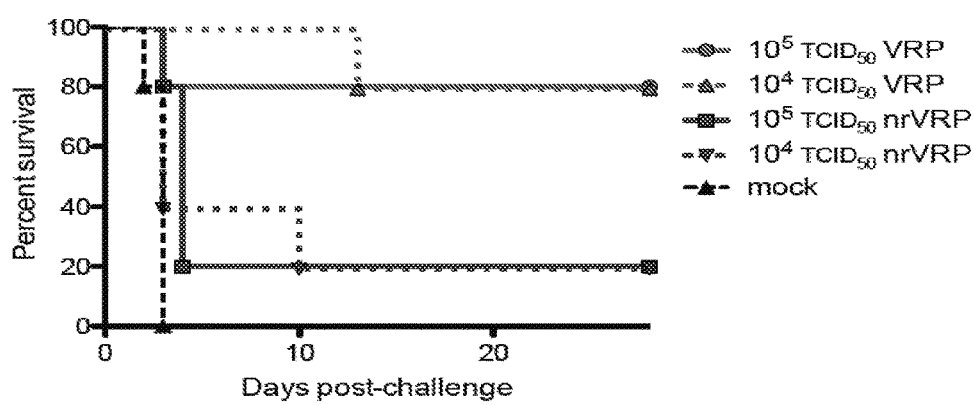
Figure 4C:
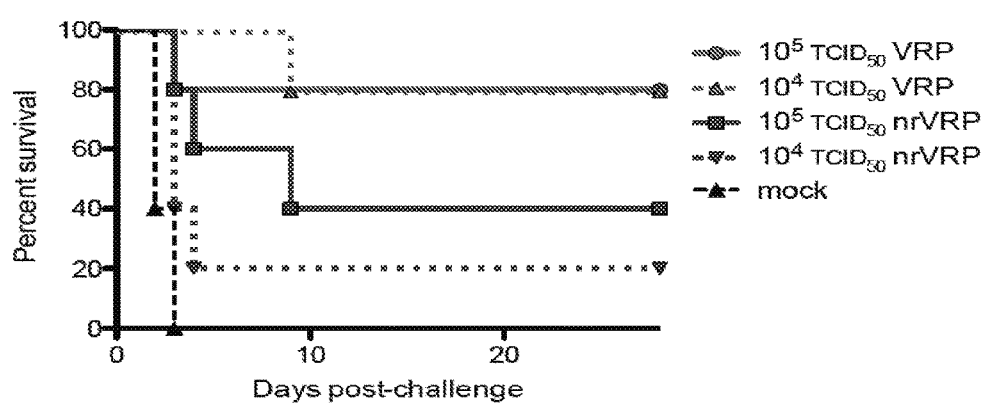

Single Dose VRP$_{RVF}$ Immunization Provides Protection from Virulent Virus Challenge by 24 Hpi To determine vaccine efficacy at early times post-immunization, mice were immunized with a single dose of $1.0 \times 10^5$ or $1.0 \times 10^4$ TCID$_{50}$ VRP$_{RVF}$, or $1.0 \times 10^5$ or $1.0 \times 10^4$ TCID$_{50}$ nr-VRP$_{RVF}$ and challenged with virulent RVFV 1, 2, 3 or 4 dpi. When challenged 24 hours after immunization, 60% of the higher dose VRP$_{RVF}$-immunized mice survived, and 80% survived challenge administered on days 2 and 3, irrespective of dose (FIGS. 4A-4C). All mice immunized with VRP$_{RVF}$ survived challenge given 4 dpi. Mice immunized with nr-VRP$_{RVF}$ displayed lower levels of protection; regardless of immunization dose, 20% of mice challenged 1 or 2 dpi survived. The highest survivorship of nr-VRP-$_{RVF}$-immunized mice observed was 40% on 3 dpi (FIGS. 4A-4C).

VRP$_{RVF}$-Immunized Mice Show Significant Upregulation in Antiviral Gene Expression Antiviral gene expression, including IFN-β, was quantified in VRP$_{RVF}$- and nr-VRP$_{RVF}$-immunized mice relative to mock-immunized mice 12 and 24 hpi. Genes significantly upregulated are shown in Table 1 (*p<0.05; **p<0.001). The only gene significantly downregulated relative to mock-immunized mice was cFOS, in the livers of VRP$_{RVF}$-immunized mice 12 hpi, and in the brains of both VRP$_{RVF}$- and nr-VRP$_{RVF}$-immunized mice 24 hpi. Several genes were significantly upregulated in only VRP$_{RVF}$-immunized mice, including CD40, CCL3, CCL5, CXCL9, CXCL10, RIG-I, IRF3, JUN, MX1, STAT1, TLR9, TNF, and TRADD. Both VRP$_{RVF}$- and nr-VRP$_{RVF}$-immunized mice had significant upregulation of IRF7, ISG15, and LGP2 genes relative to mock-immunized mice. Significant increases of Nlrp3 and CARDS were apparent in VRP$_{RVF}$-immunized mice 12 hours earlier than in nr-VRP$_{RVF}$-immunized mice. All genes upregulated in nr-VRP$_{RVF}$-relative to mock-immunized mice were also upregulated in VRP$_{RVF}$-immunized mice.

TABLE 1

Fold-change in expression of selected antiviral genes in VRP$_{RVF}$-immunized or nr-VRP$_{RVF}$-immunized relative to mock-immunized controls

| GENE | VRP$_{RVF}$ 12 h Liver | nr-VRP$_{RVF}$ 12 h Liver | VRP$_{RVF}$ 24 h Liver | nr-VRP$_{RVF}$ 24 h Liver | VRP$_{RVF}$ 12 h Brain | nr-VRP$_{RVF}$ 12 h Brain | VRP$_{RVF}$ 24 h Brain | nr-VRP$_{RVF}$ 24 h Brain |
|---|---|---|---|---|---|---|---|---|
| CARD9 | 0.8 | 0.7 | 1.2 | 1.8 * | 2.2 ** | 1.5 | 1.0 | 0.8 |
| CD40 | 2.2* | 1.6 | 1.5 | 1.0 | 1.2 | 0.9 | 1.0 | 1.1 |
| CCL3 | 0.9 | 1.0 | 3.0 * | 1.0 | 1.2 | 1.0 | 1.9 | 0.5 |
| CCL5 | 1.2 | 1.4 | 2.0 ** | 1.6 | 1.0 | 0.3 | 0.7 | 1.0 |

TABLE 1-continued

Fold-change in expression of selected antiviral genes in $VRP_{RVF}$-immunized or nr-$VRP_{RVF}$-immunized relative to mock-immunized controls

| GENE | $VRP_{RVF}$ 12 h Liver | nr-$VRP_{RVF}$ 12 h Liver | $VRP_{RVF}$ 24 h Liver | nr-$VRP_{RVF}$ 24 h Liver | $VRP_{RVF}$ 12 h Brain | nr-$VRP_{RVF}$ 12 h Brain | $VRP_{RVF}$ 24 h Brain | nr-$VRP_{RVF}$ 24 h Brain |
|---|---|---|---|---|---|---|---|---|
| CXCL9 | 1.0 | 0.8 | 4.5 * | 0.8 | 2.6 * | 3.2 | 2.4 | 0.3 |
| CXCL10 | 3.7 * | 1.8 | 3.7 * | 1.9 | 1.8 | 1.7 | 3.5 | 1.0 |
| cFOS | 0.09 * | 0.5 | 0.4 | 0.6 | 1.5 * | 1.3 | 0.4 * | 0.3 * |
| IRF3 | 0.9 | 0.9 | 0.9 | 0.6 | 2.6 ** | 1.6 | 0.4 | 0.7 |
| IRF7 | 5.0 ** | 2.1 ** | 11.2 | 3.6 ** | 3.2 | 2.2 | 6.0 | 1.3 |
| ISG15 | 16.1 * | 3.3 * | 14.1 * | 2.9 * | 1.2 | 0.9 | 6.3 | 0.6 |
| JUN | 0.4 | 0.7 | 0.4 | 1.0 | 2.6 * | 1.5 | 0.6 | 0.4 |
| LPG2 | 5.1 ** | 2.0 ** | 4.4 ** | 1.9 * | 2.7 | 2.3 | 2.3 | 1.0 |
| MX1 | 1.7 | 0.4 | 7.7 ** | 2.1 | 0.6 | 0.6 | 1.9 * | 0.8 |
| NLRP3 | 0.8 | 0.8 | 1.6 | 2.0 | 2.2 * | 1.2 | 0.4 | 0.7 |
| RIG-I | 2.0 ** | 1.0 | 1.7 | 0.8 | 0.7 | 0.9 | 2.4 | 1.0 |
| STAT1 | 2.7 ** | 1.3 | 2.6 * | 1.2 | 0.7 | 0.8 | 4.0 | 0.8 |
| TLR9 | 3.1 | 1.4 | 1.5 | 0.8 | 2.9 * | 1.3 | 0.7 | 0.8 |
| TNF | 2.7 * | 1.2 | 4.0 | 1.8 | N/A | N/A | 2.0 | 0.9 |
| TRADD | 1.1 | 1.0 | 1.0 | 1.3 | 1.6 ** | 1.2 | 0.8 | 0.9 |

Significant fold change:
*p < 0.05;
**p < 0.01

Figure 5:
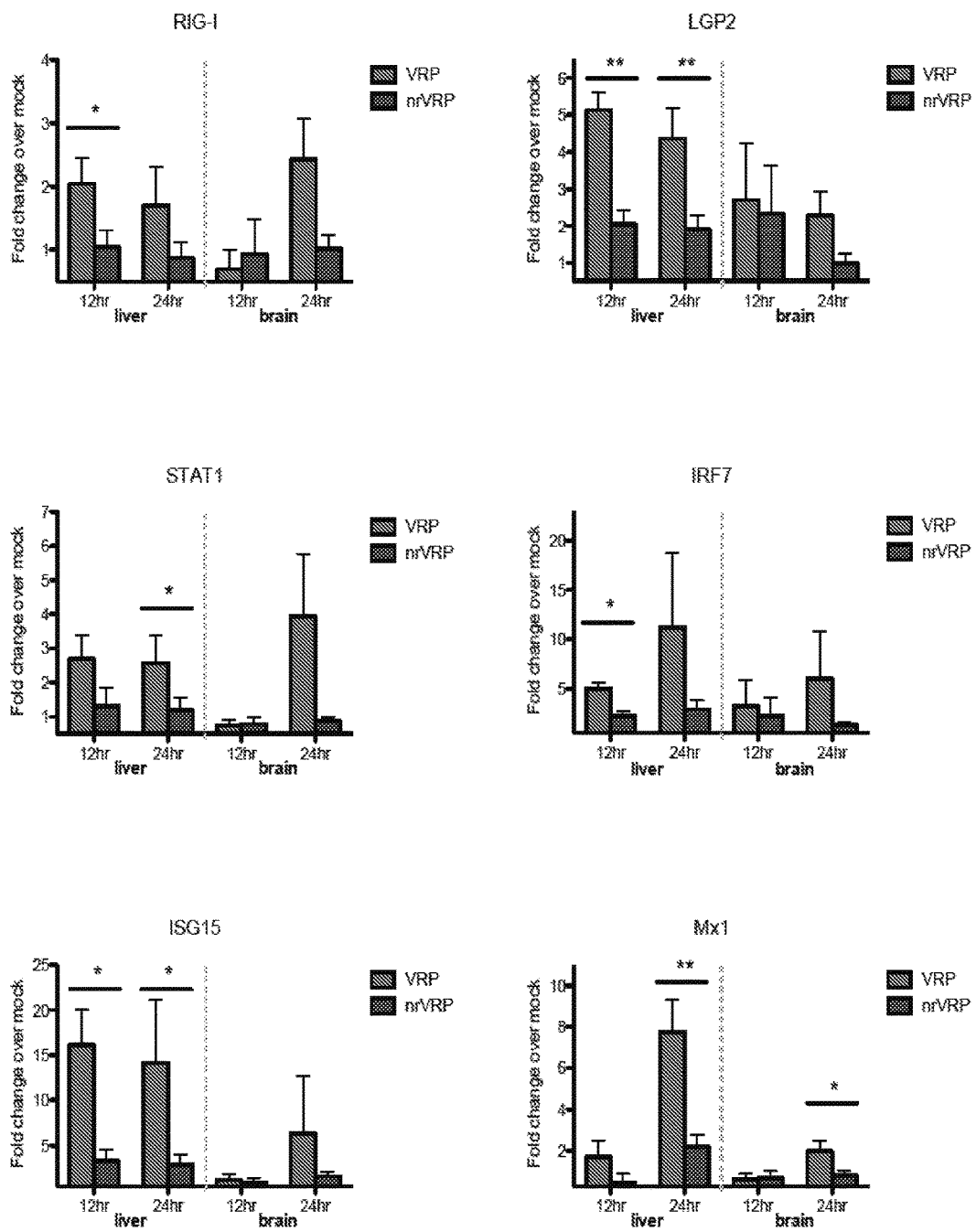
FIG. 5: $VRP_{RVF}$ stimulate significantly higher antiviral gene expression than non-replicating counterparts. The graphs show fold-change (over mock-immunized) of relevant antiviral cytokine gene expression 12-24 hours post-immunization with $VRP_{RVF}$ (left bar in each pair) or nr-$VRP_{RVF}$ (right bar in each pair). Error bars show standard deviation of fold change. Asterisks indicate significant differences between $VRP_{RVF}$ and nr-$VRP_{RVF}$ (*p<0.05; **p<0.01).
Figure 6:
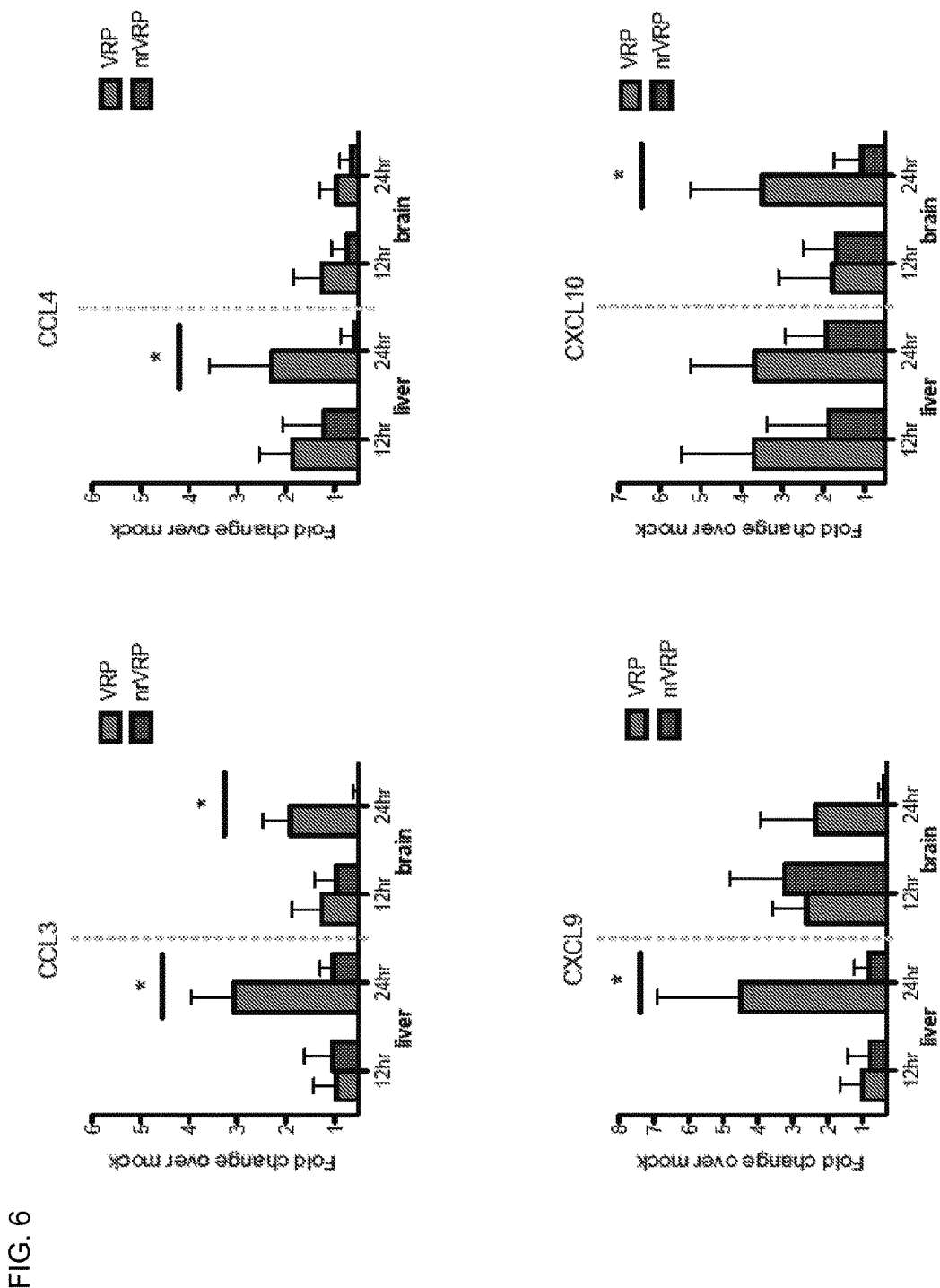
FIG. 6: $VRP_{RVF}$ stimulate significantly higher chemokine gene expression than non-replicating counterparts. The graphs show fold-change (over mock-immunized) of relevant chemokine gene expression 12-24 hours post-immunization with $VRP_{RVF}$ (left bar in each pair) or nr-$VRP_{RVF}$ (right bar in each pair). Error bars show standard deviation of fold change. Asterisk indicates significant differences between $VRP_{RVF}$ and nr-$VRP_{RVF}$ (*p<0.05).

Several genes were expressed at significantly higher levels in $VRP_{RVF}$-immunized mice relative to nr-$VRP_{RVF}$-immunized mice. In the liver, RIG-I, LGP2, IRF7, and ISG15 expression was elevated in $VRP_{RVF}$-immunized mice by 12 hpi, and STAT1 and MX1 expression was significantly higher by 24 hpi (FIG. 5). Chemokines CCL3, CCL4, and CXCL9 were significantly elevated in the livers of $VRP_{RVF}$-immunized mice by 24 hpi (FIG. 5). Also by 24 hpi, MDA5 and CXCL10 were upregulated in the brains of $VRP_{RVF}$- relative to nr-$VRP_{RVF}$-immunized mice (FIG. 5 and FIG. 6).

DISCUSSION

Large outbreaks of RVFV can have a devastating impact on human and animal health; however, there are currently no approved vaccines for use outside of the endemic areas within Africa. In these areas, widespread use of available livestock vaccines has been limited due to safety concerns or poor immunogenicity. Early live attenuated constructs were associated with abortion or teratogenesis in pregnant animals (e.g., Smithburn and MP12) (Botros et al., *J. Med. Virol.* 78:787-791, 2006; Hunter et al., *Onderstepoort J. Vet. Res.* 69:95-98, 2002). Inactivated VLP-like vaccines are much safer, but require the use of adjuvant or multiple boosters for complete protection. Recently, a rationally designed, reverse genetics-derived vaccine candidate that is safe and efficacious in livestock was developed (Bird et al., *J. Virol.* 85:12901-12909, 2011). As an additional countermeasure against RVFV, the robust efficacy of this vaccine was paired with the enhanced safety inherent in non-replicating constructs. The resulting $VRP_{RVF}$ undergo only one round of infection and are biologically confined to the initially infected cells, but can actively synthesize viral RNA and express viral nucleoprotein and polymerase.

$VRP_{RVF}$ particles are morphologically indistinguishable from wild-type virus, but lack 4 genes, those encoding virulence factors NSs and NSm and structural proteins Gn and Gc. Deletions of NSm (Bird et al., *Virology* 362:10-15, 2007) and NSs (Vialat et al., *J. Virol.* 74:1538-1543, 2010) have been shown to reduce virulence of RVFV in adult rodents. The NSs protein inhibits the host immune response to RVFV infection through multiple mechanisms (Billecocq et al., *J. Virol.* 78:9798-9806, 2004; Habjan et al., *J. Virol.* 83:4365-4375, 2009; Ikegami et al., *Ann. N. Y. Acad. Sci.* 1171 Suppl 1:E75-85, 2009; Le May et al., *Cell* 116:541-550, 2004; Le May et al., *PLoS Pathogens* 4:e13, 2008), and therefore its absence or mutation is a common feature of many RVF vaccine candidates (Bird et al., *J. Virol.* 82:2681-2691, 2008; Dungu et al., *Vaccine* 28:4581-4587, 2010). Additional full-length deletions of genes encoding the structural proteins Gn and Gc confine $VRP_{RVF}$ replication to the initially infected cells. The resulting inability to spread within the host dramatically reduces the chance of vaccine-induced pathogenicity and likely explains the safety of $VRP_{RVF}$ infections in suckling mice, particularly given the rapid and uniform mortality seen with intracranial inoculation of suckling mice with RVF viruses.

Although extremely attenuated, $VRP_{RVF}$, like RVFV, contain the polymerase and nucleoprotein, the two factors required for viral replication, allowing for viral RNA expression and de novo viral protein synthesis in the target cells. Intracellular replication of single-stranded RNA viruses (including members of the Bunyaviridae) initiates a strong innate immune response via Toll-like receptors and/or the cytoplasmic RIG-I-like helicases, culminating in the production of important antiviral proteins, including interferon (IFN) (Elliott and Weber, *Viruses* 1:1003-1021, 2009; Kawai and Akira, *Ann. N. Y Acad. Sci.* 1143:1-20, 2008). In wild-type RVFV infection, the NSs protein abolishes these host responses. However, immunization with replicating $VRP_{RVF}$ lacking the NSs would allow for unobstructed production of IFN and IFN-stimulated genes (ISGs), thus preserving critical aspects of the antiviral response. Indeed, in multiple experiments, a significantly stronger immune response and associated protective efficacy was observed in $VRP_{RVF}$-immunized mice relative to nr-$VRP_{RVF}$- and mock-immunized mice.

Mice immunized with $VRP_{RVF}$ produced significantly higher levels of total IgG and neutralizing antibodies than nr-$VRP_{RVF}$-immunized mice, and were completely protected from virulent virus challenge at 28 dpi, suggesting that replication is critical for robust immunity and subsequent protection. As early as 12 hpi, clear differences in host response were already apparent between mice immunized with $VRP_{RVF}$ and nr-$VRP_{RVF}$. Relative to both nr-$VRP_{RVF}$- and mock-immunized mice, $VRP_{RVF}$ immunization resulted in significant systemic induction of IFN-inducible genes, including STAT1, IRF7, ISG15, RIG-I, LPG2, and MDA5. These genes stimulate the expression of important players in the cellular defense against viruses, including PKR, OAS, IRFs, MX1, and MHC classes I and II (Katze et al., *Nat. Rev. Immunol.* 2:675-687, 2002). Activation of ISGs, particularly MHC, provides a mechanism for the improved antibody response and protection seen after immunization with replicating $VRP_{RVF}$. Additionally, induction of very early cell-mediated and subsequent adaptive immune responses in $VRP_{RVF}$ immunized mice was evident from the significant upregulation of CCL4 (MIP-1β) and CXCL9 (MIG) expression in the liver, and CCL3 (MIP-1α) and CXCL10 (IP-10) expression in the liver and brain. These chemokines play important roles in attracting various immune cells, including monocytes/macrophages, NK cells and T cells, and in mediating T cell activation, aiding in initiation of cell-mediated and humoral adaptive immunity.

Rapid onset of a systemic antiviral response suggested that $VRP_{RVF}$ immunization could confer early protection. $VRP_{RVF}$ were found to be highly efficacious against virulent virus challenge within days of immunization; a single dose of $VRP_{RVF}$ provided 60% protection by just 1 dpi and complete protection by 4 dpi. This early efficacy indicates that $VRP_{RVF}$ will be a valuable control measure in the field. If RVFV was introduced into an area with large naïve populations, immunization with $VRP_{RVF}$ early in the outbreak could prevent rapid viral spread throughout and beyond the affected region. Furthermore, the low genetic diversity and single serotype of the virus suggests that a $VRP_{RVF}$ vaccine would be broadly protective against all known strains of RVFV.

The efficacy of $VRP_{RVF}$ immunization against a virulent virus challenge 100,000-fold higher than the $LD_{50}$ at early and late time points was remarkable. This protection likely hinges on the ability of the $VRP_{RVF}$, administered subcutaneously and in a single dose, to elicit a robust immune response in distant tissues within hours of immunization. This systemic response to $VRP_{RVF}$ inoculation is clearly illustrated by the upregulation of antiviral genes in the liver and brain after vaccination. To explain the host-wide effect of localized $VRP_{RVF}$ immunization, it was hypothesized that immunization results in $VRP_{RVF}$ infection of resident macrophages or dendritic cells in the skin. Recent work has demonstrated that macrophages and dendritic cells are permissive to replication and are important targets of RVFV infection (Lozach et al., *Cell Host Microbe* 10:75-88, 2011; McElroy and Nichol, *Virology* 422(1):6-12, 2011; Smith et al., *Virology* 407:256-267, 2010). Given the absence of the NSs protein in the $VRP_{RVF}$ construct, active replication within these cell types should stimulate a strong IFN response, as shown in vitro (McElroy and Nichol, *Virology* 422(1):6-12, 2011), leading to a systemic antiviral response. At the time points tested in these experiments, upregulation of the tested IFN subtypes was not detected. However, IFN must clearly have been produced within the host to induce the downstream expression of ISGs that were detected in the liver and brain. The bulk of IFN synthesis may occur at the site of immunization in locally infected macrophages or dendritic cells and then be dispersed systemically. Alternatively, IFN induction might be detectable in the liver and brain only at earlier time points, or as subtypes not evaluated here. RVFV is highly sensitive to IFN, and the rapid onset of a strong IFN response associated with $VRP_{RVF}$ immunization provides a plausible explanation for early protection against challenge.

Replication-competent particles are a safe vaccine approach, much like inactivated or VLP-like constructs, yet stimulate a stronger immune response and, therefore, provide higher levels of protection from virulent challenge with just a single immunization. The data described herein show that $VRP_{RVF}$ immunization rapidly and systemically initiates a strong cytokine and chemokine response with resulting protection seen as early as 24 hours post immunization. Further, it is demonstrates that the active replication that defines $VRP_{RVF}$, and distinguishes these particles from classical VLP, is critical for strong innate and adaptive immune responses and subsequently, complete protection from challenge.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A Rift Valley fever (RVF) virus replicon particle (VRP$_{RVF}$), comprising:
   (i) RVF virus Gn and Gc glycoproteins;
   (ii) RVF virus polymerase protein;
   (iii) RVF virus nucleoprotein;
   (iv) an RVF virus L genome segment; and
   (v) an RVF virus S genome segment,
   wherein the VRP$_{RVF}$ does not contain an RVF virus M genome segment and does not contain any nucleic acid molecules encoding the Gn and Gc glycoproteins.

2. The VRP$_{RVF}$ of claim 1, wherein the S genome segment comprises a deletion of the NSs open reading frame (ORF).

3. The VRP$_{RVF}$ of claim 2, wherein the NSs ORF is replaced by an ORF encoding a heterologous protein.

4. The VRP$_{RVF}$ of claim 3, wherein the ORF encoding a heterologous protein comprises a reporter gene ORF.

5. The VRP$_{RVF}$ of claim 1, wherein the VRP$_{RVF}$ does not contain an RVF virus NSm protein.

6. The VRP$_{RVF}$ of claim 1, wherein the RVF virus is RVF virus strain ZHS01.

7. An immunogenic composition comprising the $VRP_{RVF}$ of claim 1 and a pharmaceutically acceptable carrier.

8. A method of eliciting an immune response against RVF virus in a subject, comprising administering to the subject an effective amount of the $VRP_{RVF}$ of claim 1.

9. A method of immunizing a subject against RVF virus infection, comprising administering to the subject an effective amount of the $VRP_{RVF}$ of claim 1.

10. The method of claim 8, wherein the $VRP_{RVF}$ is administered in a single dose.

11. The method of claim 8, wherein the $VRP_{RVF}$ is administered intravenously, intramuscularly or subcutaneously.

12. A method of differentiating a subject administered the $VRP_{RVF}$ of claim 1 from a subject naturally infected with RVF virus, comprising:
   obtaining a biological sample from the subject; and
   detecting the presence or absence of anti-NSm and anti-nucleoprotein antibodies in the sample, wherein the presence of both anti-nucleoprotein and anti-NSm antibodies in the sample indicates that the subject was naturally infected with RVF virus, and wherein the presence of anti-nucleoprotein antibodies and absence of anti-NSm antibodies in the sample indicates that the subject was administered the $VRP_{RVF}$.

13. A method of differentiating a subject administered the $VRP_{RVF}$ of claim 2 from a subject naturally infected with RVF virus, comprising:
   obtaining a biological sample from the subject; and
   detecting the presence or absence of anti-NS s and anti-nucleoprotein antibodies in the sample, wherein the presence of both anti-nucleoprotein and anti-NSs antibodies in the sample indicates that the subject was naturally infected with RVF virus, and wherein the presence of anti-nucleoprotein antibodies and absence of anti-NSs antibodies in the sample indicates that the subject was administered the $VRP_{RVF}$.

* * * * *

SEQUENCE LISTING

```
<160> NUMBER OF SEQ ID NOS: 3

<210> SEQ ID NO 1
<211> LENGTH: 6404
<212> TYPE: DNA
<213> ORGANISM: Artificial Sequence
<220> FEATURE:
<223> OTHER INFORMATION: Synthetic construct

<400> SEQUENCE: 1
acacaaaggc gcccaatcat ggattctata ttatcaaaac agctggttga caagactggt      60
tttgttagag tgccaatcaa gcattttgac tgtacaatgc taactctggc acttccaaca     120
tttgatgttt ccaagatggt agatagaatt accatagact tcaatctgga tgatatacaa     180
ggagcatctg aaataggctc aactttgcta ccctccatgt cgatagatgt ggaagatatg     240
gccaattttg ttcacgattt caccttttggc cacttagctg acaagactga cagactgtta     300
atgcgtgagt tccccatgat gaatgacggg tttgatcatt tgagccctga catgatcatt     360
```

```
aaaactacat ctggcatgta caacatcgtt gagttcacca cctttagggg agatgaaaga      420
ggtgcattcc aggctgccat gactaaactc gctaagtatg aggttccttg tgagaacaga      480
tctcagggca ggactgttgt tctttatgtt gttagtgctt atcggcatgg tgtatggtct      540
aatctggagc tagaggactc tgaagcagag gagatggttt ataggtacag acttgctctt      600
agtgtgatgg atgagctaag gaccttgttc ccagaactgt catccacaga tgaggaacta      660
gggaagactg agagagagtt gctagccatg gtctcctcca tccaaataaa ttggtcagtc      720
acagaatctg tgtttccacc cttcagcaga gaaatgtttg acaggtttag atcctcccct      780
cccgattcag agtatatcac gaggatagtg agcagatgcc tcataaattc tcaagagaaa      840
ctcatcaata gttccttctt tgctgaaggg aatgataagg ctctgagatt ttcaaaaaac      900
gctgaagagt gttccttggc agtagagaga gccttaaatc agtatagagc agaagacaac      960
cttagggacc tcaatgacca caagtcaact attcagctgc ctccctggct gtcctatcat     1020
gatgtcgatg gcaaagatct gtgccctctt cagggattag atgtgagagg ggaccatccc     1080
atgtgcaact tgtggaggga agtggtcacc tctgcaaacc tagaggagat tgagaggatg     1140
cacgatgatg cagcagcaga acttgagttt gctcctttcgg gagtaaagga caggccagat     1200
gagagaaaca gataccatag agtccaccta aatatgggct cagatgatag tgtctacata     1260
gctgctttag gagttaatgg aaagaagcat aaagcagaca ctttagtgca acaaatgaga     1320
gacaggagta acagcctttt ctccccagac cacgatgtgg atcacatatc tgaatttctc     1380
tctgcatgct ctagtgactt gtgggcaaca gatgaggacc tgtacaaccc tctctcttgt     1440
gataaagagc ttagattggc agcccagagg attcatcagc catccttgtc agaaaggggt     1500
ttcaatgaga tcataacaga gcactacaaa ttcatgggaa gtaggatagg ttcatggtgc     1560
caaatggtca gcttgatagg agctgagcta tcagcttctg ttaaacaaca tgtcaagcct     1620
aactactttg tgattaaacg actactaggt tctgggattt tcttgctaat caagcccact     1680
tccagcaaaa gccatatatt tgtgtctttt gcaattaagc gctcttgctg ggcctttgat     1740
ctctccactt ccagggtttt caagccctac atagatgctg gggatctgtt agttactgac     1800
tttgtttctt ataagctaag caagcttacc aacctctgca agtgcgtttc attaatggag     1860
tcctccttct cattctgggc agaagcattt ggcattccaa gctggaactt tgttggtgac     1920
ttgttcaggt cttcagactc tgcagcaatg gatgcctcat acatgggcaa actttcttta     1980
ttaacccttt tggaagacaa agcagcaact gaagagttac agactattgc aagatatata     2040
atcatggagg gctttgtctc gccccagaa atcccaaaac ctcacaagat gacctctaag     2100
tttcctaagg ttctcaggtc agagctgcag gtttacttat taaactgctt atgcagaact     2160
atccagagaa tagcaggtga gcccttcatt cttaagaaga aggatgggtc tatatcctgg     2220
ggtggcatgt tcaatccttt ttcagggcgt ccactgcttg atatgcaacc actcatcagc     2280
tgttgttaca atggttactt taaaaataaa gaagaagaga ctgagccttc gtccctttct     2340
gggatgtata agaaaatcat agaacttgag caccttagac cacagtcaga tgccttcttg     2400
ggttacaaag atccagaact tcccagaatg catgagttca gtgtttccta cttgaaggag     2460
gcttgcaatc atgctaagct agtcttgagg agcctctatg acagaatttt catggagcag     2520
atagacaacc agattattcg agagctcagt gggttgactc tagaaaggtt ggccacactt     2580
aaggccacaa gcaactttaa tgagaattgg tatgtctata aggatgtagc agacaaaaac     2640
tacacaaggg ataaattatt agtgaagatg tcaaatatg cctctgaggg aaagagccta     2700
gctatccaga agtttgagga ttgtatgagg cagatagagt cacaaggatg catgcatatt     2760
```

```
tgtttgttta agaaacaaca gcatggaggt ctgagagaga tctatgtgat gggtgcagag      2820
gaaagaattg ttcaatcggt ggtggagaca atagccaggt ccatagggaa gttctttgct      2880
tctgataccc tctgtaaccc ccccaataaa gtgaaaattc ctgagacaca tggcatcagg      2940
gcccggaagc aatgtaaggg gcctgtgtgg acttgtgcaa catcagatga tgcaaggaag      3000
tggaaccaag gccatttttgt tacaaagttt gccctcatgc tgtgtgagtt cacctctcct      3060
aaatggtggc cgctgatcat tagggggatgc tcaatgttta ccaggaaaag gatgatgatg      3120
aatttgaatt atcttaagat cctggatggt catcgggagc ttgatattag agatgacttt      3180
gtgatggatc tcttcaaagc ttatcatggc gaggcagaag ttccatgggc ctttaaaggc      3240
aaaacatatt tggaaaccac aacagggatg atgcagggaa tactgcatta tacttcctca      3300
ctattacaca ccattcacca agaatacatc cggtccttgt cctttaagat attcaacctg      3360
aaggttgctc ctgagatgag caagggcctg gtttgtgaca tgatgcaagg atcagatgat      3420
agtagtatgc taatcagctt cccagctgat gatgagaagg ttcttaccag atgcaaagtg      3480
gccgcagcta tatgcttccg catgaagaag gagctgggag tgtaccttgc catttacccc      3540
tcagagaagt ccacagcaaa cacagatttt gtgatggagt acaattctga attttatttc      3600
cacacccagc atgttagacc aacgatcagg tggattgcag cttgttgcag cctgccagaa      3660
gtggaaacac tagtagcccg ccaggaagag gcctctaacc taatgacttc agttactgag      3720
ggaggtgggt cattctcctt agctgcaatg attcagcaag ctcagtgcac tctccattac      3780
atgctgatgg gcatgggagt gtctgagcta ttcttagagt ataagaaggc agtgctgaag      3840
tggaatgacc ctggcctggg tttcttcctg cttgacaatc cttatgcgtg cggattggga      3900
ggtttcagat ttaatctctt caaagctatc accagaactg atttgcagaa gctatatgct      3960
ttcttcatga gaaggtcaa gggctcagct gctagggact gggcagatga agatgtcacc      4020
atcccagaaa cgtgtagcgt gagcccaggt ggcgctctaa ttcttagctc ctctctaaag      4080
tggggatcta ggaagaagtt tcagaaattg agagaccgtt tgaacatacc agagaactgg      4140
attgaactaa taaatgagaa tccagaggtg ctctatcggg ctcccagaac aggcccagaa      4200
atattgttgc gcattgcaga gaaagtccat agcccaggtg ttgtgtcatc attgtcttct      4260
ggcaatgcag tttgtaaagt catggcctca gctgtatact tcttatcagc aacaattttt      4320
gaggacactg gacgtcctga gttcaacttc ttggaggatt ctaagtacag cttgctacaa      4380
aagatggctg catattctgg cttttcatggt tttaatgata tggagccaga agatatatta      4440
ttcttattcc cgaatattga ggaattagaa tcactggatt ctatagttta caacaaggga      4500
gaaatagaca tcatcccaag agtcaacatc agggatgcaa cccaaaccag ggtcactatc      4560
tttaatgagc agaagaccct ccggacatct ccagagaagt tggtgtcaga caagtggttt      4620
gggactcaga agagtaggat aggcaaaaca accttcctgg ctgaatggga aaagctaaag      4680
aaaattgtaa agtggttgga agacactcca gaagcaactc tagctcacac cccactgaat      4740
aaccatattc aagttaggaa tttctttgct agaatggaaa gcaagcctag aacagtcaga      4800
ataacaggag ctccagtaaa gaagaggtca ggggttagta agatagctat ggttatccgt      4860
gacaatttct cccggatggg ccatcttcga ggtgtagaag accttgctgg cttcactcgt      4920
agtgtgtcag ctgaaattct caagcacttt ctattctgta tactacaagg tccatacagt      4980
gagagctata agctacagct aatctacaga gtcctaagct cagtgtcaaa cgttgagata      5040
aaggaatcag atggtaagac aaaaaccaac ttgattggaa tccttcagag atttctagat      5100
ggtgatcacg ttgtccccat aattgaagag atgggagccg gaacagtggg tggattcatc      5160
```

```
aagagacaac aatctaaagt tgtgcagaac aaagtggtct attatggagt tgggatttgg    5220
agaggcttca tggatggata tcaggtccat ctagagatag aaaatgacat aggacagccc    5280
ccaaggctta ggaatgtcac aactaactgt cagagcagcc catgggacct gagtattcca    5340
ataaggcaat gggcagaaga catggggtc acaaacaacc aggattattc ctctaaatct    5400
agcagagggg ccagatattg gatgcattca ttcaggatgc aaggacctag caagccattt    5460
ggatgcccag tttatattat taagggtgat atgtcagatg tcatcagact gagaaaggag    5520
gaggtggaga tgaaagtacg gggctctact ctcaacttgt acaccaagca ccattctcat    5580
caggacctac acattctatc ttacactgca tcagacaatg atctcagtcc aggcattttc    5640
aagtcaatat cagatgaggg ggtggctcaa gccctgcaat tatttgagag ggagccaagc    5700
aactgctggg tgagatgtga gtctgtagcc ccaaaattta tatcagccat ccttgagata    5760
tgtgagggga agagacagat aagggggaatt aacagaacca gactctcaga gattgtgaga    5820
atttgttctg aatcttccct aagatcaaaa gtcggatcta tgttctcatt tgtcgccaat    5880
gtcgaggagg cccatgatgt tgattatgat gcgttaatgg atctaatgat agaggatgcc    5940
aagaacaatg cattcagtca tgttgttgac tgcatagagt tggatgttag tggcccttac    6000
gagatggagt cttttgatac atctgatgtc aatctctttg gccagcccca ttacaaggac    6060
atcagttcat tatctatgat tgctcatccc ttaatggata agtttgttga ttatgctatt    6120
tctaagatgg ggagagcctc agttaggaaa gttctagaaa caggtcggtg ctccagcaaa    6180
gactatgatt tatcaaaggt tctcttcaga actctacaga gaccagaaga aagcattagg    6240
atagatgatc tggaattata tgaggagaca gatgtggcgg atgacatgct aggctaagac    6300
caataagcaa agtcaggctt agatttaggg atactatgct agtattggaa tccatgtggg    6360
ttctgatact agcatagtgc tacaatattg ggcggtcttt gtgt                    6404
```

<210> SEQ ID NO 2
<211> LENGTH: 1630
<212> TYPE: DNA
<213> ORGANISM: Artificial Sequence
<220> FEATURE:
<223> OTHER INFORMATION: Synthetic construct

<400> SEQUENCE: 2

```
acacaaagct ccctagagat acaaacacta ttacaataat ggacaactat caagagcttg      60
cgatccagtt tgctgctcaa gcagtggacc gcaatgagat tgaacagtgg gtccgagagt     120
ttgcttatca agggtttgat gcccgtagag ttatcgaact cttaaagcag tatggtgggg     180
ctgactggga gaaggatgcc aagaaaatga ttgttctggc tctaactcgt ggcaacaagc     240
ccaggaggat gatgataaaa atgtcgaaag aaggcaaagc aactgtggag ctctctcatca    300 acaagtataa gctaaaggaa gggaatcctt cccgggatga gttgactcta tcacgagttg     360
ctgccgccct ggctggctgg acatgccagg ctttggtcgt cttgagtgag tggcttcctg     420
tcactgggac taccatggac ggcctatccc ctgcatacc aaggcatatg atgcaccca     480 gctttgctgg catggtggat ccttctctac caggagacta tctaagggca atattagatg     540
ctcactctct gtatctgctg cagttctccc gggtcatcaa cccaaacctc cgaggtagaa     600
caaaagagga ggttgctgca acgttcacgc agccaatgaa tgcagcagtg aatagcaact     660
ttataagcca tgagaagagg agagaattct tgaaagcctt tggacttgtg gattctaatg     720
ggaagccgtc agctgctgtc atggcagccg ctcaggctta caagacagca gcctaagtgg     780
ctgcccaggg ggttgggggg aaggggagtt ggggttacgg tcgggattgg ggggtgggg     840
```

| | |
|---|---:|
| gtggggcagc cttaacctct aatcagatct ttacttgtac agctcgtcca tgccgagagt | 900 |
| gatcccggcg gcggtcacga actccagcag gaccatgtga tcgcgcttct cgttggggtc | 960 |
| tttgctcagg gcggactggg tgctcaggta gtggttgtcg ggcagcagca cggggccgtc | 1020 |
| gccgatgggg gtgttctgct ggtagtggtc ggcgagctgc acgctgccgt cctcgatgtt | 1080 |
| gtggcggatc ttgaagttca ccttgatgcc gttcttctgc ttgtcggcca tgatatagac | 1140 |
| gttgtggctg ttgtagttgt actccagctt gtgcccagg atgttgccgt cctccttgaa | 1200 |
| gtcgatgccc ttcagctcga tgcggttcac cagggtgtcg ccctcgaact tcacctcggc | 1260 |
| gcgggtcttg tagttgccgt cgtccttgaa aagatggtg cgctcctgga cgtagccttc | 1320 |
| gggcatggcg gacttgaaga agtcgtgctg cttcatgtgg tcggggtagc ggctgaagca | 1380 |
| ctgcacgccg taggtcaggg tggtcacgag ggtgggccag ggcacgggca gcttgccggt | 1440 |
| ggtgcagatg aacttcaggg tcagcttgcc gtaggtggca tcgccctcgc cctcgccgga | 1500 |
| cacgctgaac ttgtggccgt ttacgtcgcc gtccagctcg accaggatgg gcaccacccc | 1560 |
| ggtgaacagc tcctcgccct tgctcaccat ggtaccgata tacttgataa gcactagggg | 1620 |
| gtctttgtgt | 1630 |

<210> SEQ ID NO 3
<211> LENGTH: 3207
<212> TYPE: DNA
<213> ORGANISM: Artificial Sequence
<220> FEATURE:
<223> OTHER INFORMATION: Synthetic construct

<400> SEQUENCE: 3

| | |
|---|---:|
| accatggcag ggattgcaat gacagtcctt ccagccttag cagtttttgc tttggcacct | 60 |
| gttgttttg ctgaagaccc ccatctcaga aacagaccag ggaaggggca caactacatt | 120 |
| gacgggatga ctcaggagga tgccacatgc aaacctgtga catatgctgg ggcatgtagc | 180 |
| agttttgatg tcttgcttga aagggaaaa tttcccctt tccagtcgta tgctcatcat | 240 |
| agaactctac tagaggcagt tcacgacacc atcattgcaa aggctgatcc acctagctgt | 300 |
| gaccttcaga gtgctcatgg gaaccccctgc atgaaagaga actcgtgat gaagacacac | 360 |
| tgtccaaatg actaccagtc agctcattac ctcaacaatg acgggaaaat ggcttcagtc | 420 |
| aagtgccctc ctaagtatga gctcactgag gactgcaact tttgtaggca gatgacaggt | 480 |
| gctagcctga agaagggggtc ttatcctctc caagacttgt tttgtcagtc aagtgaggat | 540 |
| gatggatcaa aattaaaaac aaaaatgaaa ggggtctgcg aagtgggggt tcaagcactc | 600 |
| aaaaagtgtg atggccaact cagcactgca catgaggttg tgccctttgc agtgtttaag | 660 |
| aactcaaaga aggtttatct tgataagctt gaccttaaga ctgaggagaa tctgctacca | 720 |
| gactcatttg tctgtttcga gcataaggga cagtacaaag aacaatggga ctctggtcag | 780 |
| actaagaggg agctcaaaag cttttgatatc tctcagtgcc ccaagattgg aggacatggt | 840 |
| agtaagaagt gcactgggga cgcagcattt tgctctgctt atgagtgcac tgctcagtac | 900 |
| gccaatgcct attgttcaca tgctaatggg tcagggattg tgcagataca agtatcaggg | 960 |
| gtctggaaga agcctttatg tgtagggtat gagagagtgg ttgtgaagag agaactctct | 1020 |
| gccaagccca tccagagagt tgagccttgc acaacttgta taaccaaatg tgagcctcat | 1080 |
| ggattggttg tccgatcaac agggttcaag atatcatcag cagttgcttg tgctagcgga | 1140 |
| gtttgcgtca caggatcgca gagtcctcc accgagatta cactcaagta tccagggata | 1200 |
| tcccagtctt ctgggggga catagggggtt cacatggcac acgatgatca gtcagttagc | 1260 |

```
tccaaaatag tagctcactg ccctccccag gacccgtgtt tagtgcatgg ctgcatagtg    1320
tgtgctcatg gcctgataaa ttaccagtgt cacactgctc tcagtgcctt tgttgttgtg    1380
tttgtattca gttctattgc aataatttgt ttagctgttc tttataggt gcttaagtgc     1440 ctgaagattg ccccaaggaa agttctgaat ccactaatgt ggatcacagc cttcatcaga    1500
tggatatata agaagatggt tgccagagtg gcagacaaca ttaatcaagt gaacagggaa    1560
ataggatgga tggaaggagg tcagttggtt ctagggaacc ctgcccctat tcctcgtcat    1620
gccccaatcc cacgttatag cacatacctg atgttattat tgattgtctc atatgcatca    1680
gcatgttcag aactgattca ggcaagctcc agaatcacca cttgctctac agagggtgtt    1740
aacaccaagt gtagactgtc tggcacagca ttgatcagag cagggtcagt tggggcagag    1800
gcttgtttga tgttgaaggg ggtcaaggaa gatcaaacca agttcttaaa gataaaaact    1860
gtctcaagtg agctatcatg cagggagggc cagagttatt ggactgggtc ctttagccct    1920
aaatgtttga gctcaaggag atgccacctt gtcggggaat gccatgtgaa taggtgtctg    1980
tcttggaggg acaatgaaac ttcagcagag ttttcatttg ttggggaaag cacgaccatg    2040
cgagagaata agtgttttga gcaatgtgga ggatgggggt gtgggtgttt caatgtgaac    2100
ccatcttgct tatttgtgca cacgtatctg cagtcagtta gaaaagaggc cttagagtt     2160 tttaactgta tcgactgggt gcataaactc actctagaga tcacagactt tgatggctct    2220
gtttcaacaa tagacttggg agcatcatct agccgtttca caaactgggg ttcagttagc    2280
ctctcactgg acgcagaggg catctcaggc tcaaatagct tttctttcat tgagagccca    2340 ggtaaaggt atgcaattgt tgatgagcca ttctcagaaa ttcctcggca agggttcttg     2400
ggggagatca ggtgcaattc agagtcctca gtcctgagtg ctcatgaatc atgccttagg    2460
gcaccaaacc ttatctcata caagcccatg atagatcaat tggagtgcac aacaaatctg    2520
attgatccct ttgttgtctt tgagagggt tctctgccac agacaaggaa tgataaaacc       2580
tttgcagctt caaaaggaaa tagaggtgtt caagctttct ctaagggctc tgtacaagct    2640
gatctaactc tgatgtttga caattttgag gtggactttg tgggagcagc cgtatcttgt    2700
gatgccgcct tcttaaattt gacaggttgc tattcttgca atgcaggggc cagggtctgc    2760
ctgtctatca catccacagg aactggatct ctctctgccc acaataagga tgggtctctg    2820
catatagtcc ttccatcaga gaatggaaca aaagaccagt gtcagatact acacttcact    2880
gtgcctgaag tagaggagga gtttatgtac tcttgtgatg gagatgagcg gcctctgttg    2940
gtgaagggga ccctgatagc cattgatcca tttgatgata ggcgggaagc aggggggaa     3000 tcaacagttg tgaatccaaa atctggatct tggaatttct ttgactggtt ttctggactc    3060
atgagttggt ttggagggcc tcttaaaact atactcctca tttgcctgta tgttgcatta    3120
tcaattgggc tcttttcct ccttatatat cttggaagaa caggcctctc taaaatgtgg     3180
cttgctgcca ctaagaaggc ctcatag                                        3207
```